United States Patent [19]

Hughes

[11] Patent Number: 5,187,167
[45] Date of Patent: Feb. 16, 1993

[54] PHARMACEUTICAL COMPOSITIONS COMPRISING QUINAZOLIN-4-ONE DERIVATIVES

[75] Inventor: Leslie R. Hughes, MacClesfield, England

[73] Assignee: Imperial Chemical Industries Plc, London, England

[21] Appl. No.: 775,102

[22] Filed: Oct. 11, 1991

Related U.S. Application Data

[60] Division of Ser. No. 577,579, Sep. 5, 1990, Pat. No. 5,081,124, which is a division of Ser. No. 334,748, Apr. 6, 1989, Pat. No. 4,992,550, which is a continuation of Ser. No. 30,424, Mar. 26, 1987, abandoned.

[30] Foreign Application Priority Data

Mar. 27, 1986 [GB] United Kingdom ............... 8607683

[51] Int. Cl.$^5$ .................... A01N 43/48; A61K 31/165
[52] U.S. Cl. ...................................... 514/259; 514/306
[58] Field of Search ............................... 514/259, 306

[56] References Cited

U.S. PATENT DOCUMENTS 4,564,616 1/1986 Jones et al. ..................... 514/260

OTHER PUBLICATIONS

Jones et al. in "Anticancer Quinazoline-Substituted Amino Acids", CA 106(13) 102,679c, May, 1986.

*Primary Examiner*—Nathan M. Nutter
*Assistant Examiner*—Jeffrey Culpeper Mullis
*Attorney, Agent, or Firm*—Cushman, Darby & Cushman

[57] ABSTRACT

A quinazoline of the formula:-

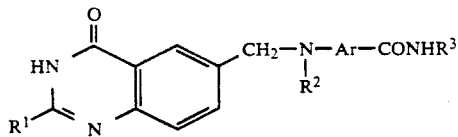

wherein $R^1$ is alkyl, cycloalkyl, alkenyl, alkynyl, alkoxy, alkylthio, aryl, aryloxy, arylalkyl, halogeno, hydroxy, mercapto, pyridylthio, pyrimidinylthio, or substituted alkyl or alkoxy;

wherein $R^2$ is hydrogen, alkyl, alkenyl, alkynyl, substituted alkyl or alkanoyl;

wherein Ar is phenylene, naphthylene or heterocyclene which is unsubstituted or bears one or more substituents and wherein $R^3$ is such that $R^3-NH_2$ is an amino acid; or a pharmaceutically-acceptable salt or ester thereof. The compounds possess anti-tumor activity.

10 Claims, No Drawings

PHARMACEUTICAL COMPOSITIONS COMPRISING QUINAZOLIN-4-ONE DERIVATIVES

This is a division of application Ser. No. 07/577,579, filed Sept. 5, 1990, now U.S. Pat. No. 5,081,124, which is a divisional of 07/334,748, filed Apr. 6, 1989, now U.S. Pat. No. 4,992,550, which is a continuation of Ser. No. 07/030,424, filed Nov. 26, 1987, abandoned.

This invention relates to novel anti-tumour agents and more particularly it relates to quinazoline derivatives which possess anti-tumour activity.

One group of anti-tumour agents comprises the antimetabolites which are antagonists of folic acid, such as aminopterin and methotrexate. A newer compound of this type which showed considerable promise in clinical trials is known as CB3717 and is described and claimed in United Kingdom Patent Specification No. 2065653B. Despite its promise, however, CB3717 shows symptoms of toxicity in humans, particularly in relation to the liver and kidney.

Compounds of this type are believed to act as anti-tumour agents by inhibiting the enzyme thymidylate synthetase. Their anti-tumour activity may be assessed in vitro by determining their inhibitory effect on that enzyme, and in cell cultures by their inhibitory effect on the cell line L1210.

We have now found that certain quinazoline derivatives are considerably more active than CB3717, and furthermore are more water-soluble than that compound, which may be clinically important by increasing the ease of clearance through the kidney thereby decreasing any symptoms of toxicity.

According to the invention there is provided a quinazoline of the formula:

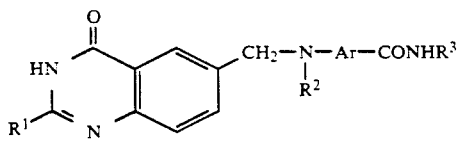

wherein $R^1$ is alkyl, cycloalkyl, alkenyl, alkynyl, alkoxy or alkylthio each of up to 6 carbon atoms; aryl, aryloxy or arylalkyl each of up to 10 carbon atoms; halogeno, hydroxy, mercapto, pyridylthio or pyrimidinylthio; alkyl of up to 3 carbon atoms which bears one or more substituents selected from halogeno, hydroxy, amino, pyridylthio, pyrimidinylthio, alkoxy, alkanoyloxy, alkylthio, alkylamino, dialkylamino and alkanoylamino each of up to 6 carbon atoms and aroyloxy and aroylamino each of up to 10 carbon atoms; or alkoxy of up to 3 carbon atoms which bears one or more substituents selected from hydroxy and alkoxy of up to 6 carbon atoms; wherein $R^2$ is hydrogen, alkyl, alkenyl, alkynyl, hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl or alkanoyl each of up to 6 carbon atoms or aroylalkyl of up to 10 carbon atoms; wherein Ar is phenylene, naphthylene or heterocyclene which is unsubstituted or which bears one or more substituents selected from halogeno, phenyl, cyano, nitro, hydroxy, amino and carbamoyl and alkyl, alkoxy, halogenoalkyl, alkanoylamino, alkylthio and alkoxycarbonyl each of up to 6 carbon atoms; and wherein $R^3$ is such that $R^3$—$NH_2$ is an amino acid; or a pharmaceutically-acceptable salt or ester thereof.

A suitable value for $R^1$ or $R^2$ when it is alkyl or for an alkyl substituent in Ar is, for example, methyl, ethyl, propyl, isopropyl, isobutyl, tert-butyl, pentyl or hexyl.

A suitable value for $R^1$ when it is cycloalkyl is, for example, cyclopropyl, cyclopentyl or cyclohexyl.

A suitable value for $R^1$ or $R^2$ when it is alkenyl is, for example, prop-2-enyl, but-2-enyl, but-3-enyl, 2-methylprop-2-enyl, hex-2-enyl, hex-5-enyl or 2,3-dimethylbut-2-enyl.

A suitable value for $R^1$ or $R^2$ when it is alkynyl is, for example, prop-2-ynyl, but-2-ynyl, but-3-ynyl, pent-2-ynyl, 3-methylpent-4-ynyl, hex-2-ynyl or hex-5-ynyl.

A suitable value for $R^1$ when it is alkoxy, alkylthio or for an alkoxy or alkylthio substituent in Ar is, for example, methoxy, ethoxy, isopropoxy, hexyloxy, methylthio, isopropylthio or hexylthio.

A suitable value for $R^1$ when it is aryl or arylalkyl is, for example, phenyl, tolyl, benzyl, α-methylbenzyl or phenethyl.

A suitable value for $R^1$ when it is aryloxy is, for example, phenoxy or tolyloxy.

A suitable value for $R^1$ when it is halogeno is, for example, fluoro, chloro, bromo or iodo.

A suitable value for $R^1$ when it is substituted alkyl is, for example, fluoromethyl, difluoromethyl, trifluoromethyl, 2-fluoroethyl, 3-fluoropropyl, chloromethyl, dichloromethyl, hydroxymethyl, 2-hydroxyethyl, 3-hydroxypropyl, aminomethyl, 3-aminopropyl, pyrid-2-ylthiomethyl, pyrimidin-2-ylthiomethyl, methoxymethyl, isopropoxymethyl, 3-methoxypropyl, acetoxymethyl, propionyloxymethyl, methylthiomethyl, 2-methylthiopropyl, propylthiomethyl, methylaminomethyl, propylaminomethyl, methylaminopropyl, dimethylaminomethyl, diethylaminomethyl, ethylmethylaminomethyl, 3-dimethylaminopropyl, acetamidomethyl, 3-acetamidopropyl, propionamidomethyl, benzoyloxymethyl or benzamidomethyl.

A suitable value for $R^1$ when it is substituted alkoxy is, for example, 2-hydroxyethoxy, 4-hydroxybutoxy, 3-hydroxy-2-methylpropoxy, 2-methoxyethoxy, 3-methoxypropoxy or 2-ethoxyethoxy.

A suitable value for $R^2$ when it is hydroxyalkyl, alkoxyalkyl, mercaptoalkyl or alkylthioalkyl is, for example, 2-hydroxyethyl, 3-hydroxypropyl, 2-methoxyethyl, 2-ethoxyethyl, 3-methoxypropyl, 2-methoxypropyl, 2-mercaptoethyl, 3-mercaptopropyl, 2-methylthioethyl, 3-methylthiopropyl or 2-ethylthioethyl.

A suitable value for $R^2$ when it is halogenoalkyl, cyanoalkyl, aminoalkyl, alkylaminoalkyl or dialkylaminoalkyl is, for example, 2-fluoroethyl, 2-chloroethyl, 2-bromoethyl, 3-fluoropropyl, 3-chloropropyl, cyanomethyl, 2-cyanoethyl, 3-cyanopropyl, 2-aminoethyl, 3-aminopropyl, 3-amino-2-methylpropyl, 2-methylaminoethyl, 2-dimethylaminoethyl, 2-ethylaminoethyl, 2-diethylaminoethyl, 3-methylaminopropyl or 3-dimethylaminopropyl.

A suitable value for $R^2$ when it is alkanoylalkyl, carboxyalkyl, carbamoylalkyl or alkanoyl is, for example, acetonyl, 2-acetylethyl, propionylmethyl, 2-propionylethyl, 3-acetylpropyl, 4-acetylbutyl, carboxymethyl, 2-carboxyethyl, carbamoylmethyl, acetyl, propionyl or butyryl.

A suitable value for $R^2$ when it is aroylalkyl is, for example, phenacyl or 2-benzoylethyl.

A suitable value for Ar when it is heterocyclene is, for example, a 5-membered or 6-membered aromatic (that is, fully unsaturated) heterocyclene diradical which contains up to 2 heteroatoms selected from the group consisting of oxygen, nitrogen and sulphur, for example, thienylene, pyridylene, pyrimidinylene, thiazolylene or oxazolylene.

A suitable halogeno, halogenoalkyl, alkanoylamino or alkoxycarbonyl substituent in Ar is, for example, fluoro, chloro, bromo, iodo, fluoromethyl, difluoromethyl, trifluoromethyl, acetamido, propionamido, isopropionamido, methoxycarbonyl, ethoxycarbonyl or isobutoxycarbonyl.

A suitable value for $R^3$ is such that $R^3$—$NH_2$ is a naturally-occurring amino-acid such as L-aspartic acid, L-glutamic acid, L-alanine, L-phenylalanine, L-serine, glycine or L-ornithine. Alternatively $R^3$ may be such that $R^3$—$NH_2$ is L-2-aminobutyric acid or a poly-L-glutamic acid. $R^3$ may therefore have, for example, the formula:

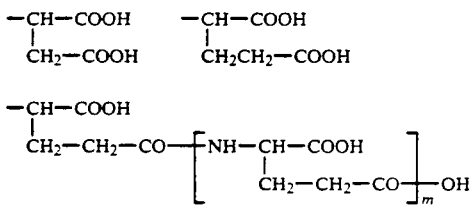

wherein m is an integer from 1 to 10, or the formula:

A suitable pharmaceutically-acceptable salt of a quinazoline of the invention is, for example, an acid addition salt with, for example, inorganic or organic acids, for example hydrochloric, hydrobromic, trifluoroacetic or maleic acid; or an alkali metal, for example sodium, alkaline earth metal or ammonium, for example tetra(2-hydroxyethyl)ammonium, salt.

A suitable pharmaceutically-acceptable ester of a quinazoline of the invention is, for example, an ester with an aliphatic alcohol of up to 6 carbon atoms, for example a methyl, ethyl or tert-butyl ester.

It is to be understood that when $R^3$ contains two carboxylic acid residues, that is, when it is derived from, for example, aspartic or glutamic acid, a salt or ester may be a mono-acid-mono-salt or ester or it may be a di-salt or ester.

A preferred quinazoline of the invention has the formula stated above wherein $R^1$ is methyl, ethyl, prop-2-enyl, prop-2-ynyl, methoxy, methylthio, phenyl, benzyl, fluoromethyl, difluoromethyl, trifluoromethyl, hydroxymethyl, aminomethyl, methoxymethyl, acetoxymethyl, methylthiomethyl, methylaminomethyl, dimethylaminomethyl or acetamidomethyl; wherein $R^2$ is hydrogen, methyl, ethyl, propyl, prop-2-enyl, prop-2-ynyl, 2-hydroxyethyl, 2-methoxyethyl, 2-mercaptoethyl, 2-methylthioethyl, 2-aminoethyl, 2-methylaminoethyl, 2-dimethylaminoethyl, 2-bromoethyl or acetyl; wherein Ar is 1,4-phenylene or thien-2,5-diyl which is unsubstituted or which bears one substituent selected from chloro, methyl, methoxy or trifluoromethyl and wherein $R^3$ is such that $R^3$—$NH_2$ is L-alanine, L-glutamic acid or L-aspartic acid.

A further preferred quinazoline of the invention has the formula stated above wherein $R^1$ is methyl, ethyl, isopropyl, cyclopropyl, cyclohexyl, methoxy, ethoxy, phenoxy, fluoro, chloro, hydroxy, mercapto, pyrimidin-2-ylthio, pyrimidin-2-ylthiomethyl, 2-hydroxyethoxy or 2-methoxyethoxy; wherein $R^2$ is hydrogen, methyl, ethyl, prop-2-ynyl, 3-hydroxypropyl, 3-methoxypropyl, 2-fluoroethyl, cyanomethyl, acetonyl, carboxymethyl or carbamoylmethyl; wherein Ar is 1,4-phenylene, thien-2,5-diyl, pyrid-2,5-diyl, pyrimidin-2,5-diyl, thiazol-2,5-diyl or oxazol-2,5-diyl which is unsubstituted or which bears one substituent selected from fluoro, chloro, cyano, nitro, hydroxy, amino or acetamido and wherein $R^3$ is such that $R^3$—$NH_2$ is L-glutamic acid, glycine, L-phenylalanine, L-serine, L-ornithine or L-aspartic acid.

An especially preferred quinazoline of the invention has the formula stated above wherein $R^1$ is methyl, ethyl, methoxy, fluoromethyl or hydroxymethyl; wherein $R^2$ is hydrogen, methyl, ethyl, propyl, prop-2-enyl, prop-2-ynyl or 2-hydroxyethyl; wherein Ar is 1,4-phenylene or thien-2,5-diyl and wherein $R^3$ is such that $R^3$—$NH_2$ is L-glutamic acid.

A further especially preferred quinazoline of the invention has the formula stated above wherein $R^1$ is methyl, methoxy, fluoromethyl or hydroxymethyl; wherein $R^2$ is hydrogen, methyl, ethyl, prop-2-ynyl, 3-hydroxypropyl, 2-fluoroethyl or acetonyl; wherein Ar is 1,4-phenylene, thien-2,5-diyl, pyrid-2,5-diyl or 2-fluoro-1,4-phenylene and wherein $R^3$ is such that $R^3$—$NH_2$ is L-glutamic acid.

Specific particularly preferred quinazolines of the invention form the group of compounds:

N-p-[N-(3,4-dihydro-2-methyl-4-oxoquinazolin-6-ylmethyl)-N-(prop-2-ynyl)amino]benzoyl-L-glutamic acid, N-p-[N-(3,4-dihydro-2-methyl-4-oxoquinazolin-6-ylmethyl)-N-methylamino]benzoyl-L-glutamic acid, N-p-[N-(2-ethyl-3,4-dihydro-4-oxoquinazolin-6-ylmethyl)-N-(prop-2-ynyl)amino]benzoyl-L-glutamic acid, N-p-[N-(3,4-dihydro-2-methyl-4-oxoquinazolin-6-ylmethyl)-N-methylamino]-o-fluorobenzoyl-L-glutamic acid, N-p-[N-(3,4-dihydro-2-methyl-4-oxoquinazolin-6-ylmethyl)-N-ethylamino]-o-fluorobenzoyl-L-glutamic acid, N-p-[N-(3,4-dihydro-2-methyl-4-oxoquinazolin-6-ylmethyl)-N-(prop-2-ynyl)amino]-o-fluorobenzoyl-L-glutamic acid;

N-{5-[N-(3,4-dihydro-2-methyl-4-oxoquinazolin-6-ylmethyl)-N-methylamino]-2-thenoyl}-L-glutamic acid, N-{5-[N-(3,4-dihydro-2-methyl-4-oxoquinazolin-6-ylmethyl)-N-ethylamino]-2-thenoyl}-L-glutamic acid, N-{5-[N-(3,4-dihydro-2-methyl-4-oxoquinazolin-6-ylmethyl)-N-(prop-2-ynyl)amino]picolinoyl}-L-glutamic acid, N-p-[N-(3,4-dihydro-2-methyl-4-oxoquinazolin-6-ylmethyl)-N-(2-fluoroethyl)amino]benzoyl-L-glutamic acid, N-p-[N-(3,4-dihydro-2-methoxy-4-oxoquinazolin-6-ylmethyl)-N-(prop-2-ynyl)amino]benzoyl-L-glutamic acid, N-p-[N-(3,4-dihydro-2-hydroxymethyl-4-oxoquinazolin-6-ylmethyl)-N-(prop-2-ynyl)amino]benzoyl-L-glutamic acid, N-p-[N-(3,4-dihydro-2-hydroxymethyl-4-oxoquinazolin-6-ylmethyl)-N-ethylamino]benzoyl-L-glutamic acid, N-p-[N-(2-fluoromethyl-3,4-dihydro-4-oxoquinazolin-6-ylmethyl)-N-(prop-2-ynyl)amino]benzoyl-L-glutamic acid and N-p-[N-(2-fluoromethyl-3,4-dihydro-4-oxoquinazolin-6-ylmethyl)-N-ethylamino]benzoyl-L-glutamic acid.

A quinazoline of the invention may be prepared by any process known to be applicable to the preparation of chemically-related compounds.

A preferred process for the manufacture of a quinazoline of the invention comprises the reaction of a compound of the formula:

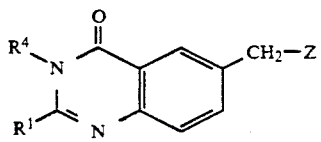

wherein $R^1$ has the meaning stated above, provided that when $R^1$ is hydroxyalkyl, aminoalkyl, alkylaminoalkyl or hydroxyalkoxy the hydroxy and amino groups are protected by conventional protecting group, $R^4$ is hydrogen or a protecting group and Z is a displaceable group, with a compound of the formula:

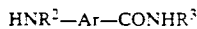

wherein $R^2$, Ar and $R^3$ have the meanings stated above, provided that when $R^2$ is hydroxyalkyl, mercaptoalkyl, aminoalkyl, alkylaminoalkyl or carboxyalkyl, when there is an amino or hydroxy group in Ar or when there is an amino, hydroxy or carboxy group in $R^3$, any mercapto, amino and carboxy group is protected by a conventional protecting group and any hydroxy group may be protected by a conventional protecting group or alternatively any hydroxy group need not be protected; whereafter any undesired protecting group in $R^1$, $R^2$, $R^3$ and Ar is removed.

A suitable protecting group for a hydroxy group is, for example, an esterifying group, for example an acetyl or benzoyl group, which may be removed by hydrolysis with a base, for example sodium hydroxide, or provided that $R^1$ and $R^2$ do not contain an alkenyl or alkynyl group, the protecting group may be, for example, an α-arylalkyl group, for example a benzyl group, which may be removed by hydrogenation over a catalyst, for example palladium-on-charcoal.

A suitable protecting group for a mercapto group is, for example, an esterifying group, for example an acetyl group, which may be removed by hydrolysis with a base, for example sodium hydroxide.

A suitable protecting group for an amino group may be, for example, an alkoxycarbonyl group, for example a tert-butyloxycarbonyl group which may be removed by treatment with an organic acid, for example trifluoroacetic acid; or it may be, for example, a benzyloxycarbonyl group which may be removed by treatment with a Lewis acid, for example boron tris(trifluoroacetate).

A suitable alternative protecting group for a primary amino group is, for example, a phthaloyl group which may be removed by treatment with an alkylamine, for example dimethylaminopropylamine or with hydrazine.

A suitable protecting group for a carboxy group may be an esterifying group, for example a methyl or an ethyl group which may be removed by hydrolysis with a base, for example sodium hydroxide; or, for example a tert-butyl group which may be removed by treatment with an organic acid, for example trifluoroacetic acid.

A suitable value for $R^4$ when it is a protecting group is, for example, a pivaloyloxymethyl group which may be removed by hydrolysis with a base, for example sodium hydroxide Z may be, for example, a halogeno or sulphonyloxy group, for example a chloro, bromo, methanesulphonyloxy or toluene-p-sulphonyloxy group.

The protecting group for the various carboxy groups in $R^3$ may be esterifying groups such as permit the product, after removal of the optional protecting group $R^4$ and of any undesired protecting groups in $R^1$, $R^2$, $R^3$ or Ar, to fall within the definition of a quinazoline of the invention. In such instance the carboxy protecting groups in $R^3$ may be removed or they may be retained. Alternatively a different protecting group may be used which will be removed.

A further preferred process for the manufacture of a quinazoline of the invention comprises the reaction of an acid of the formula:

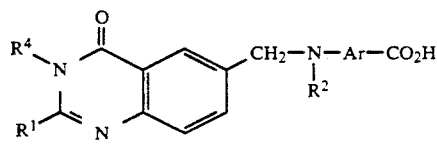

or a reactive derivative thereof, with a compound of the formula $R^3$—$NH_2$, wherein $R^1$, $R^2$, $R^3$, $R^4$ and Ar have the meanings stated above and any mercapto, amino, alkylamino and carboxy group in $R^1$, $R^2$, $R^3$ and Ar is protected by a conventional protecting group, as stated above, and any hydroxy group in $R^1$, $R^2$, $R^3$ and Ar may be protected by a conventional protecting group, as stated above or alternatively any hydroxy group need not be protected; whereafter the protecting groups are removed by conventional means.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an acyl azide, for example an azide formed by the reaction of the acid and an azide such as diphenylphosphoryl azide; or the product of the reaction of the acid and a carbodiimide, for example dicyclohexylcarbodiimide.

The carboxylic acid used as starting material may be obtained by the reaction of a compound of the formula

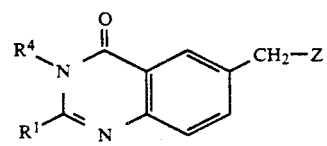

wherein $R^1$, $R^4$ and Z have the meanings stated above, with a compound of the formula:

HNR²—Ar—CO₂R⁵ wherein $R^2$ and Ar have the meanings stated above and $R^5$ is a protecting group which can be removed to provide a carboxylic acid.

$R^5$ may be, for example, a methyl or an ethyl group which may be removed by hydrolysis with a base, for example sodium hydroxide or $R^5$ may be, for example, a tert-butyl group which may be removed by cleavage with an organic acid, for example trifluoroacetic acid.

The protecting group for the carboxy group in $R^5$ may be, for example, an esterifying group which can be removed while the protecting group for any mercapto, amino, carboxy and hydroxy group in $R^1$, $R^2$ and Ar is retained.

A further preferred process for the manufacture of a quinazoline of the invention, wherein $R^1$ is alkoxy, aryloxy or alkoxy of up to 3 carbon atoms which bears one or more substituents selected from hydroxy and alkoxy, comprises the reaction of a compound of the formula:

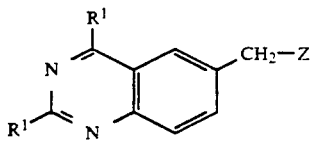

wherein $R^1$ has the last-mentioned meaning stated above, provided that when there is a hydroxy substituent in $R^1$ it is protected by a conventional protecting group, as stated above, and Z is a displaceable group, with a compound of the formula:

HNR²—Ar—CONHR³ wherein $R^2$, $R^3$ and Ar have the meanings stated above, provided that when $R^2$ is hydroxyalkyl, mercaptoalkyl, aminoalkyl, alkylaminoalkyl or carboxyalkyl, when there is an amino or hydroxy group in Ar or when there is an amino, hydroxy or carboxy group in $R^3$, any mercapto, amino and carboxy group is protected by a conventional protecting group, as stated above, and any hydroxy group may be protected by a conventional protecting group, as stated above or alternatively any hydroxy group need not be protected; whereafter the protecting groups are removed by conventional means, as stated above and the $R^1$ group situated at the 4-position of the quinazoline ring is removed by hydrolysis with a base, for example sodium hydroxide, to form a quinazoline of the invention.

A further preferred process for the manufacture of a quinazoline of the invention, wherein $R^1$ is mercapto, alkylthio, pyridylthio or pyrimidinylthio, comprises the reaction of a quinazoline of the formula:

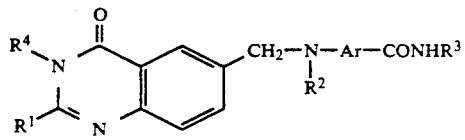

wherein $R^1$ is halogeno or halogenoalkyl and $R^2$, $R^3$, $R^4$ and Ar have the meanings stated above, provided that when $R^2$ is mercaptoalkyl, hydroxyalkyl, aminoalkyl, alkylaminoalkyl or carboxyalkyl, when there is an amino or hydroxy group in Ar or when there is an amino, hydroxy or carboxy group in $R^3$, any mercapto, amino, carboxy and hydroxy group may be protected by a conventional protecting group, as stated above or alternatively any amino, carboxy and hydroxy group need not be protected; with thiourea to provide a compound wherein $R^1$ is mercapto; or with an alkyl, pyridyl or pyrimidinyl thiol to provide a compound wherein $R^1$ is alkylthio, pyridylthio, pyrimidinylthio, alkylthioalkyl, pyridylthioalkyl or pyrimidinylthioalkyl; whereafter the protecting groups are removed by conventional means, as stated above.

A further preferred process for the manufacture of a quinazoline of the invention, wherein $R^1$ is alkylthio, comprises the reaction of a quinazoline of the formula:

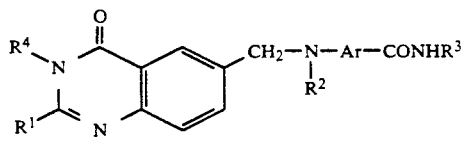

wherein $R^1$ is mercapto and $R^2$, $R^3$, $R^4$ and Ar have the meanings stated above, provided that when $R^2$ is hydroxyalkyl, mercaptoalkyl, aminoalkyl, alkylaminoalkyl or carboxyalkyl, when there is an amino or hydroxy group in Ar or when there is an amino, hydroxy or carboxy group in $R^3$, any mercapto, amino, carboxy and hydroxy group may be protected by a conventional protecting group, as stated above or alternatively any amino, carboxyl and hydroxy group need not be protected; with a base, for example ammonium hydroxide and the resultant thiolate salt is alkylated with an alkyl halide, for example methyl iodide, to provide a compound wherein $R^1$ is alkylthio, for example methylthio; whereafter the protecting groups, if present, are removed by conventional means, as stated above.

As stated above a quinazoline of the invention possesses anti-tumour activity and may itself be active thus or it may be a pro-drug which is converted in vivo to an active compound. Preferred quinazolines of the invention are 50 to 500 times more active than CB3717 in inhibiting the growth of the L1210 cell-line. L1210 is a mouse leukaemia cell line which can be grown in tissue culture (UK Patent Specification No. 2065653B).

The quinazoline of the invention may be administered to a warm-blooded animal, including a human, in the form of a pharmaceutical composition which comprises the quinazoline in association with a pharmaceutically-acceptable diluent or carrier.

The composition may be in a form suitable for oral administration, as a tablet or capsule, or, especially, for parenteral injection, as a sterile solution, suspension or emulsion, or for topical administration, as an ointment or cream, or for rectal administration as a suppository.

The composition may contain, in addition to the quinazoline of the invention, one or more other antitumour substances selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

The quinazoline will normally be administered to a warm-blooded animal at a dose within the range 50-5000 mg per square meter body area of the animal.

The invention is illustrated but not limited by the following Examples:

The structures of all compounds of the invention were confirmed by proton magnetic resonance and mass spectroscopy and by elemental analysis. Proton magnetic resonance spectra were determined using a Jeol FX 90Q or a Bruker AM200 spectrometer operating at a field strength of 200 MHz. Chemical shifts are reported in parts per million downfield from tetramethylsilane as an internal standard ($\delta$ scale) and peak multiplicities are shown thus: s, singlet; d, doublet; d of d's, doublet of doublets; t, triplet; m, multiplet. Fast-atom bombardment (FAB) mass spectral data were obtained using a VG Analytical MS9 spectrometer and xenon gas and, where appropriate, either positive ion data or negative ion data were collected.

Column chromatography was performed using Merck Art 9385 silica gel.

EXAMPLE 1

A mixture of 6-bromomethyl-3,4-dihydro-2-methyl-3-pivaloyloxymethylquinazolin-4-one (0.3 g), diethyl N-(p-prop-2-ynylaminobenzoyl)-L-glutamate (UK Patent Specification No. 2065653B; 0.295 g), calcium carbonate (0.491 g) and dimethylformamide (10 ml) was stirred at 50° C. for 18 hours, cooled and filtered through a filter-aid. The filtrate was evaporated to dryness and the residual oil was purified by chromatography on a silica gel (Merck 9385) column using a 3:1 v/v mixture of methylene chloride and ethyl acetate as eluent.

A mixture of the product (0.306 g), ethanol (5 ml) and aqueous N-sodium hydroxide solution (1.42 ml) was stirred at laboratory temperature for 18 hours, acidified with acetic acid and aqueous 2N-hydrochloric acid (0.5 ml) was added. The mixture was centrifuged and the solid residue was washed three times each with water and diethyl ether (10 ml each time) and dried. There was thus obtained N-p-[N-(3,4-dihydro-2-methyl-4-oxoquinazolin-6-ylmethyl)-N-(prop-2-ynyl)amino]benzoyl-L-glutamic acid (70 mg), m.p. (powder to glass) 165° C.

NMR Spectrum: (CD$_3$SOCD$_3$) 2.0 (m, 2H, CH$_2$), 2.35 (broad t, 2H, CH$_2$CO$_2$H), 2.35 (s, 3H, CH$_3$), 3.15 (t, 1H, C≡CH, J=2 Hz), 4.3 (m, 3H, NHCH and CH$_2$C≡CH), 4.8 (s, 2H, CH$_2$N), 6.83 (d, 2H, aromatic, J=9 Hz), 7.52 (d, 1H, 8-H, J=9 Hz), 7.68 (d of d's, 1H, 7-H, J=2 and 9 Hz), 7.75 (d, 2H, aromatic, J=9 Hz), 7.97 (d, 1H, 5-H, J=2 Hz), 8.18 (d, 1H, NH, J=8 Hz), 12.15 (broad s, 1H, NH):

Mass Spectrum: (positive ion FAB) m/e 477 (P+1); Elemental Analysis: Found C, 58.9; H, 5.1; N, 10.9; C$_{25}$H$_{24}$N$_4$O$_6$.2H$_2$O requires C, 58.6; H, 5.5; N, 10.9%.

The quinazolinone used as starting material was obtained as follows:

Sodium hydride (1.08 g) was added to a stirred suspension of 3,4-dihydro-2,6-dimethylquinazolin-4-one (J. Indian Chem. Soc., 1962, 39, 369; 3.0 g) in dimethylformamide (50 ml) and the mixture was stirred at laboratory temperature for 1 hour. A solution of chloromethyl pivalate (3.36 g) in dimethylformamide (10 ml) was added and the mixture was stirred at laboratory temperature for 18 hours and then poured into saturated aqueous sodium chloride solution (200 ml). The mixture was extracted four times with diethyl ether (50 ml each time) and the combined extracts were dried and evaporated to dryness. The residue was purified by chromatography on a silica gel column using a 9:1 v/v mixture of methylene chloride and ethyl acetate as eluent. The product was crystallised from petroleum ether (b.p. 60°-80° C.) and there was thus obtained 3,4-dihydro-2,6-dimethyl-3-pivaloyloxymethyl-quinazolin-4-one (0.92 g), m.p. 98°-100° C.

A mixture of the above compound (0.92 g), N-bromosuccinimide (0.624 g), benzoyl peroxide (0.025 g) and carbon tetrachloride (50 ml) was heated under reflux for 2 hours, cooled and poured through a column of florisil (25 g). The column was eluted with carbon tetrachloride and the eluate was evaporated to dryness. There was thus obtained as solid residue 6-bromomethyl-3,4-dihydro-2-methyl-3-pivaloyloxymethylquinazolin-4-one (1.16 g), m.p. 144°-145° C.

EXAMPLE 2

The process described in Example 1 was repeated using diethyl N-(p-ethylaminobenzoyl)-L-glutamate (British Journal of Cancer, 1979, 40, 318) as starting material in place of the prop-2-ynylamino compound. There was thus obtained N-p-[N-(3,4-dihydro-2-methyl-4-oxoquinazolin-6-ylmethyl)-N-ethylamino]benzoyl-L-glutamic acid, m.p. 221°-225° C.

The process described in Example 1 was also repeated using 6-bromomethyl-3,4-dihydro-3-pivaloyloxymethyl-2-trifluoromethylquinazolin-4-one as starting material in place of the 6-bromomethyl-2-methylquinazolin-4-one. There was thus obtained N-p-[N-(3,4-dihydro-4-oxo-2-trifluoromethylquinazolin-6-ylmethyl)-N-(prop-2-ynyl)amino]benzoyl-L-glutamic acid, m.p. 110°-115° C.

3,4-Dihydro-6-methyl-2-trifluoromethylquinazolin-4-one used as starting material was prepared by reacting trifluoroacetamide and 2-amino-5-methylbenzoic acid using the method given in 'The Chemistry of Heterocyclic Compounds', Volume 24, p74.

EXAMPLE 3

A mixture of 6-bromomethyl-3,4-dihydro-2-methylquinazolin-4-one (5.1 g), diethyl N-(p-methylaminobenzoyl)-L-glutamate (Journal of Heterocyclic Chemistry, 1975, 12, 1283; 6.7 g), 2,6-lutidine (7 ml) and dry dimethylformamide (40 ml) was stirred at 80° C. under an atmosphere of argon for 18 hours. The mixture was cooled, poured into water (300 ml) and extracted with ethyl acetate (4×150 ml). The combined extracts were washed with water (2×200 ml), with a saturated aqueous sodium chloride solution (2×100 ml), dried over magnesium sulphate, filtered and evaporated. The residue was purified by chromatography on a silica gel column using ethyl acetate as eluent.

A mixture of the product (4.1 g), ethanol (25 ml) and aqueous N-sodium hydroxide solution (24.3 ml) was stirred at laboratory temperature under an atmosphere of argon for 3 hours. The mixture was evaporated to dryness, the residue was dissolved in de-ionised water and the solution was acidified to pH 2 by adding 2N-hydrochloride acid solution. The mixture was centrifuged and the solid residue was washed three times with water, diethyl ether and acetone (20 ml each time) and dried. There was thus obtained N-p-[N-(3,4-dihydro-2-methyl-4-oxoquinazolin-6-ylmethyl)-N-methylamino]- benzoyl-L-glutamic acid (containing 0.75 equivalents of water; 3 g), m.p. 254°–257° C. (decomposes).

NMR Spectrum: (CD$_3$SOCD$_3$), 2.0 (m, 2H, CH$_2$), 2.35 (broad t, 2H, C$\underline{H}_2$CO$_2$H), 2.35 (s, 3H, CH$_3$), 3.12 (s, 3H, CH$_3$N), 4.38 (m, 1H, NHC$\underline{H}$, 4.78 (s, 2H, CH$_2$N), 6.77 (d, 2H, aromatic, J=9 Hz), 7.53 (d, 1H, 8-H, J=9 Hz), 7.62 (d, of d's, 1H, 7-H, J=2 and 9 Hz), 7.73 (d, 2H, aromatic, J=9 Hz), 7.88 (d, 1H, 5-H, J=2 Hz), 8.15 (d, 1H, NH, J=8 Hz), 12.2 (s, 1H, NH);

Mass Spectrum: (positive ion FAB) m/e 453 (P+1); Elemental Analysis: Found C, 59.1; H, 5.2; N, 11.9; C$_{23}$H$_{24}$N$_4$O$_6$. 0.75 H$_2$O requires C, 59.3; H, 5.5; N, 12.0%.

The quinazolinone used as starting material was obtained as follows:

A mixture of 3,4-dihydro-2,6-dimethylquinazolin-4-one (20 g), N-bromosuccinimide (21.3 g), benzoyl peroxide (100 mg) and chloroform (600 ml) was heated to 50° C. for 6 hours during which time the mixture was illuminated by the light from a 250 Watt light bulb. The mixture was cooled. The precipitated product was separated by filtration of the mixture, washed with chloroform (2×50 ml) and dried. There was thus obtained 6-bromomethyl-3,4-dihydro-2-methylquinazolin-4-one, m.p.>330° C.

EXAMPLE 4

The process described in Example 3 was repeated using the appropriate 6-bromomethyl-3,4-dihydroquinazolin-4-one and the appropriate diethyl p-aminobenzoyl-L-glutamate as starting materials. There were thus obtained the compounds described in the following table, the structures of which were confirmed by proton magnetic resonance and mass spectroscopy and by elemental analysis.

(Journal of Medicinal Chemistry, 1985, 28, 1468 or the European Journal of Cancer, 1981, 17, 11).

Note (2): The required diethyl glutamate was prepared by reaction of diethyl p-aminobenzoyl-L-glutamate with the alkylating agents 2-acetoxyethyl bromide, 2-methoxyethyl bromide, 3-methoxypropyl bromide and 1-bromoacetone in an analogous process to that described in the literature (Journal of Medicinal Chemistry 1985, 28, 1468).

Note (3): The required quinazolinones were obtained using the method described in 'The Chemistry of Heterocyclic Compounds' Volume 24, page 74 with propionamide and isobutyramide respectively instead of acetamide as the starting material.

Note (4): The required quinazolinones were prepared by the method described in the literature (J. Amer. Chem. Soc. 1946, 68, 1299 and UK Patent Specification No. 1410178).

Note (5): 2-Acetoxymethyl-3,4-dihydro-6-methylquinazolin-4-one (Dissertationes Pharmaceuticae et Pharmacologicae 1968, 20, 29) and the appropriate diethyl p-aminobenzoyl-L-glutamate were taken through the process described in Example 3. Basic hydrolysis cleaved the glutamate esters and the acetoxy group.

Note (6): 2-Chloromethyl-3,4-dihydro-6-methylquinazolin-4-one (Dissertationes Pharmaceuticae et Pharmacologicae 1968, 20, 29) was treated with a saturated aqueous solution of ammonia at laboratory temperature for 20 hours. The solvent was removed and the product was acetylated to give 2-acetamidomethyl-3,4-dihydro-6-methylquinazolin-4-one which was used as the starting material in the sequence described in Example 3.

Note (7): 2-Chloro-3,4-dihydro-6-methylquinazolin-4-one was obtained as described in U.S. Pat. No. 4,085,213.

TABLE I

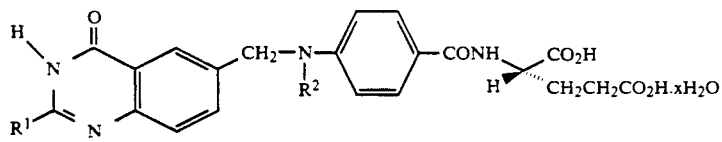

EXAMPLE 4

| Compound No | R$^1$ | (Note) | R$^2$ | m.p. | x |
|---|---|---|---|---|---|
| 1 | methyl | (1) | H | 197–20. C. | 1 |
| 2 | methyl | (1) | prop-2-enyl | 188° C. (dec.) | 1.5 |
| 3 | methyl | (1) | 3-hydroxypropyl | >300° C. (dec.) | 1.2 |
| 4 | methyl | (1) | 2-fluoroethyl | 207–210° C. | 1.2 |
| 5 | methyl | (2) | 2-hydroxyethyl | >300° C. (dec.) | 1.5 |
| 6 | methyl | (2) | 2-methoxyethyl | 248° C. (dec.) | 1.0 |
| 7 | methyl | (2) | 3-methoxypropyl | 260° C. (dec.) | 1.0 |
| 8 | methyl | (2) | acetonyl | 155–157° C. | 1.0 |
| 9 | ethyl | (3) | prop-2-ynyl | 150–157° C. | 0.5 |
| 10 | ethyl | (3) | H | 156–166° C. | 2 |
| 11 | isopropyl | (3) | prop-2-ynyl | 148–150° C. | 2 |
| 12 | phenyl | (4) | prop-2-ynyl | 170° C. | 0.5 |
| 13 | difluoromethyl | (4) | prop-2-ynyl | 135–140° C. | 1 |
| 14 | hydroxymethyl | (5) | prop-2-ynyl | 137–143° C. | 2 |
| 15 | hydroxymethyl | (5) | prop-2-enyl | 150–160° C. | 1 |
| 16 | hydroxymethyl | (5) | ethyl | 140–150° C. | 1 |
| 17 | hydroxymethyl | (5) | methyl | 194–197° C. | 1 |
| 18 | hydroxymethyl | (5) | 2-hydroxyethyl | 150–155° C. | 1 |
| 19 | hydroxymethyl | (5) | 2-fluoroethyl | 215–222° C. | 0.5 |
| 20 | acetamidomethyl | (6) | prop-2-ynyl | 229–240° C. | 1.5 |
| 21 | chloro | (7) | prop-2-ynyl | 156–160° C. | 3 |

Note (1): The appropriate diethyl p-aminobenzoyl-L-glutamate was obtained as described in the literature

EXAMPLE 5

A mixture of 6-bromomethyl-2-fluoromethyl-3,4-dihydroquinazolin-4-one (0.62 g), di-tert-butyl N-(p-prop-2-ynylaminobenzoyl)-L-glutamate (1.2 g, prepared by reaction of di-tert-butyl N-p-aminobenzoyl-L-glutamate, known from the Journal of Medicinal Chemistry, 1985, 28, 1468, with prop-2-ynyl bromide using the method described in the European Journal of Cancer 1981, 17, 11), 2,6-lutidine (1.5 g) and dry dimethylformamide (20 ml) was stirred at 60° C. for 18 hours under an atmosphere of argon. The mixture was cooled, the solvent was evaporated and the residual oil was purified by chromatography on a florisil column using a 2:1 v/v mixture of methylene chloride and ethyl acetate as eluent.

A mixture of the product (0.6 g), trifluoroacetic acid (2 ml) and chloroform (6 ml) was stirred at laboratory temperature for 4 hours. The mixture was poured into diethyl ether (40 ml) and stirred for 10 minutes. The precipitated solid was separated by filtration of the mixture and the solid was washed with ether (3 × 10 ml) and dried. There was thus obtained N-p-[N-(2-fluoromethyl-3,4-dihydro-4-oxoquinazolin-6-ylmethyl)-N-(prop-2-ynyl)amino]benzoyl-L-glutamic acid as a dihydrate, trifluoroacetic acid salt, (0.3 g), m.p. 126°–131° C.

NMR Spectrum: ($CD_3SOCD_3$) 2.0 (m, 2H, $CH_2$), 2.3 (t, 2H, $\underline{CH_2}CO_2H$, J=6.5 Hz), 3.18 (t, 1H, C≡CH, J=2 Hz), 4.15 (m, 3H, NHCH and $CH_2C\equiv CH$), 4.8 (s, 2H, $CH_2N$), 5.27 (d, 2H, $\overline{FCH_2}$, J=47 Hz), 6.84 (d, 2H, aromatic, J=9 Hz), 7.66 (d, 1H, 8-H, J=9 Hz), 7.75 (m, 3H, aromatic and 7-H), 8.04 (d, 1H, 5-H, J=2 Hz), 8.21 (d, 1H, NH, J=8 Hz).

Mass Spectrum: (negative ion FAB) m/e 493 (P-1) Elemental Analysis: Found C, 50.5; H, 4.1; N, 9.2; $C_{25}H_{23}FN_4O_6 \cdot CF_3CO_2H \cdot 2H_2O$ requires C, 50.3; H, 4.3; N, 8.7%.

The quinazolinone used as starting material was obtained as follows:

A mixture of 2-amino-5-methylbenzoic acid (20 g) and fluoroacetamide (40 g) was heated to 120° C. for 1 hour, to 140° C. for 90 minutes and to 180° C. for 90 minutes. The mixture was cooled to room temperature and the residue was purified by chromatography on a silica gel column using a 1:1 v/v mixture of methylene chloride and ethyl acetate as eluent.

A mixture of the 2-fluoromethyl-3,4-dihydro-6-methylquinazolin-4-one (2 g) so obtained, N-bromosuccinimide (1.8 g), benzoyl peroxide (10 mg) and chloroform (50 ml) was heated to reflux for 4 hours, cooled and evaporated. The product, 6-bromomethyl-2-fluoromethyl-3,4-dihydroquinazolin-4-one was used without further purification.

The process described above was repeated using ditert-butyl N-(p-ethylaminobenzoyl)-L-glutamate (prepared by reaction of di-tert-butyl N-p-aminobenzoyl-L-glutamate with ethyl iodide using the method described above in the first paragraph of this Example) in place of the prop-2-ynylamino compound. There was thus obtained N-p-[N-(2-fluoromethyl-3,4-dihydro-4-oxoquinazolin-6-ylmethyl)-N-ethylamino]benzoyl-L-glutamic acid as a hemi-trifluoroacetic acid salt, m.p. 162°–167° C.

EXAMPLE 6

A mixture of 6-bromomethyl-3,4-dihydro-2-methylquinazolin-4-one (prepared as described in Example 3 above, 0.38 g), diethyl N-(2-fluoro-4-methylaminobenzoyl)-L-glutamate (prepared by the reaction of diethyl N-(4-amino-2-fluorobenzoyl)-L-glutamate, known from UK Patent Specification No. 2175903, with methyl iodide using the method described in the European Journal of Cancer, 1981, 17, 11; 0.7 g), powdered calcium carbonate (0.3 g) and dry dimethylformamide (2.7 ml) was stirred at 100° C. for 7 hours. The mixture was evaporated and the residue was purified by chromatography on a silica gel column using a 20:1 v/v mixture of methylene chloride and ethanol as eluent.

A mixture of the product (0.54 g), ethanol (10 ml), water (10 ml) and aqueous N-sodium hydroxide solution (6.2 ml) was stirred at laboratory temperature for 7 hours. The mixture was concentrated to a volume of approximately 5 ml, filtered and acidified to pH 3 by adding 2N-hydrochloric acid solution. The precipitated solid was isolated by centrifugation, washed with water (4 × 30 ml) and dried. There was thus obtained N-p-[N(3,4-dihydro-2-methyl-4-oxoquinazolin-6-ylmethyl)-N-methylamino]-o-fluorobenzoyl-L-glutamic acid monohydrate (0.41 g), m.p. 224°–226° C.

EXAMPLE 7

The process described in Example 6 was repeated using the appropriate diethyl L-glutamate as starting material. There were thus obtained the compounds described in the following table, the structures of which were confirmed by proton magnetic resonance and mass spectroscopy and by elemental analysis.

TABLE II

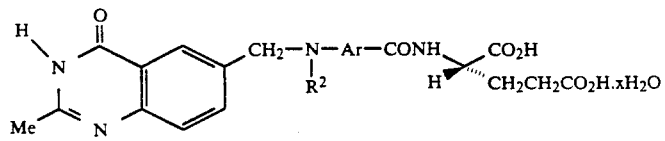

| EXAMPLE 7 Compound No. | $R^2$ | (Note) | Ar | x | m.p. |
| --- | --- | --- | --- | --- | --- |
| 1 | H | (1) | 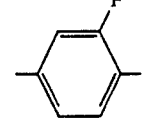 | 1 | 190–194° C. |

TABLE II-continued

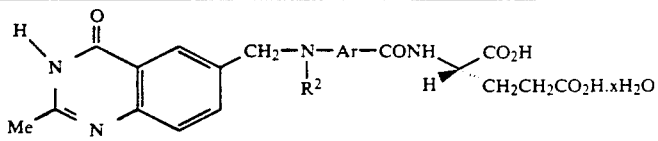

EXAMPLE 7

| Compound No. | R² | (Note) | Ar | x | m.p. |
|---|---|---|---|---|---|
| 2 | ethyl | (2) | 2-F-phenyl | 0.75 | 214–217° C. |
| 3 | prop-2-ynyl | (2) | 2-F-phenyl | 1 | 228–230° C. |
| 4 | HOCH₂CH₂ | (2) | 2-F-phenyl | 0 | 190–196° C. |
| 5 | FCH₂CH₂ | (2) | 2-F-phenyl | 0.7 | 220–225° C. |
| 6 | H₂NCOCH₂ | (3) | 2-F-phenyl | 1 | 170–185° C. |
| 7 | prop-2-ynyl | (4) | thien-2,5-diyl | 0.5 | 215–225° C. |
| 8 | methyl | (5) | thien-2,5-diyl | 1 | 180–184° C. |
| 9 | ethyl | (5) | thien-2,5-diyl | 0.75 | 162–167° C. |
| 10 | n-propyl | (5) | thien-2,5-diyl | 2 | 184–185° C. |
| 11 | methyl | (6) | pyridinyl | 0.75 | 203–205° C. |
| 12 | prop-2-ynyl | (7) | pyridinyl | 0.5 | 240–248° C. |
| 13 | methyl | (8) | pyridinyl | 2.5 | 200–204° C. |

Note (1): The preparation of diethyl N-(4-amino-2-fluorobenzoyl)-L-glutamate is described in UK Patent Specification No. 2175903.

Note (2): The appropriate diethyl glutamate was prepared by the reaction of diethyl N-(4-amino-2-fluorobenzoyl)-L-glutamate (UK Patent Specification No. 2175903) with ethyl iodide, propargyl bromide, 2-acetoxyethyl bromide or 2-fluoroethyl bromide respectively, using the method described in the Journal of Medicinal Chemistry, 1985, 28, 1468.

Note (3): Diethyl N-p-(N-cyanomethylamino)-o-fluorobenzoyl-L-glutamate was prepared by the method given in Note (2) above using chloroacetonitrile as the alkylating agent. During the final step of the process described in Example 6 the N-cyanomethylamino group was hydrolysed to an N-carbamoylmethylamino group.

Note (4): 2,6-Lutidine was used in place of calcium carbonate. Diethyl N-[5-(prop-2-ynylamino)-2-thenoyl]-L-glutamate used as starting material was obtained as follows:

Pyridine (1.5 g) was added to a mixture of 5-nitro-2-thenoyl chloride (3 g) and diethyl L-glutamate hydrochloride (4.2 g) in toluene (50 ml). The mixture was stirred at laboratory temperature for 72 hours, poured into water (200 ml) and extracted with ethyl acetate (3×100 ml). The combined extracts were washed with water (2×500 ml) and with a saturated aqueous sodium chloride solution (1×50 ml), dried over magnesium sulphate, filtered and evaporated to dryness. The residue was purified by chromatography on a silica gel column using a 9:1 v/v mixture of methylene chloride and ethyl acetate as eluent.

A mixture of the product (3.4 g), ethanol (15 ml) and an aqueous solution of sodium dithionite (6.2 g of the dihydrate salt in 30 ml of water) was stirred at 50° C. for 1 hour, poured into water (100 ml) and extracted with ethyl acetate (3×50 ml). The combined extracts were washed with a saturated aqueous sodium chloride solution (1×50 ml), dried over magnesium sulphate, filtered and evaporated to dryness. The residue was purified by chromatography on a silica gel column using a 7:3 v/v mixture of methylene chloride and ethyl acetate as eluent. There was thus obtained diethyl 5-amino-2-thenoyl-L-glutamate (1 g).

A mixture of the product (1 g), propargyl bromide (0.66 g of an 80% solution in toluene), 2,6-lutidine (0.5 g) and dimethylformamide (25 ml) was stirred at 50° C. for 24 hours, cooled, poured into water (25 ml) and extracted with ethyl acetate (3×50 ml). The combined extracts were washed with water (2×25 ml) and with a saturated aqueous sodium chloride solution (25 ml), dried over magnesium sulphate, filtered and evaporated to dryness. The residue was purified by chromatography on a silica gel column using a 7:3 v/v mixture of methylene chloride and ethyl acetate as eluent. There was thus obtained diethyl N-[5-(prop-2-ynylamino)-2-thenoyl]-L-glutamate (0.6 g).

Note (5): 2,6-Lutidine was used in place of calcium carbonate. The appropriate diethyl L-glutamate was obtained using diethyl 5-amino-2-thenoyl-L-glutamate as starting material in the process described in the last paragraph of note (4) above except that methyl iodide, ethyl iodide and n-propyl iodide respectively were used in place of propargyl bromide.

Note (6): Diethyl N-[5-(methylamino)picolinoyl]-L-glutamate used as starting material was prepared as follows:-A mixture of methyl 5-(N-tert-butoxycarbonyl-N-methylamino)picolinate (prepared using the method described in the Journal of Medicinal Chemistry, 1980, 23, 1405 except that methyl iodide was used in place of 3-trifluoromethylbenzyl chloride; 1.13 g), aqueous N-sodium hydroxide solution (8.5 ml), water (21 ml) and ethanol (15 ml) was stirred at laboratory temperature for 16 hours. The mixture was concentrated to a volume of 5 ml, acidified to pH 4 with 2N-hydrochloric acid solution and extracted with ethyl acetate (2×40 ml). The combined extracts were dried over magnesium sulphate, filtered and evaporated to give 5-(N-tert-butoxycarbonyl-N-methylamino)picolinic acid (0.8 g).

A mixture of the acid (0.74 g), oxalyl chloride (0.38 ml), methylene chloride (8 ml) and dimethylformamide was stirred at laboratory temperature for 45 minutes and evaporated to dryness. A solution of the residue in methylene chloride (10 ml) was added to a mixture of diethyl L-glutamate hydrochloride (0.77 g), 2,6-lutidine (0.65 ml) and methylene chloride (10 ml). The mixture was stirred at laboratory temperature for 16 hours, washed with N-hydrochloric acid solution, a saturated aqueous sodium bicarbonate solution and a saturated aqueous sodium chloride solution, dried over magnesium sulphate, filtered and evaporated to dryness. The residue was purified by chromatography on a silica gel column using a 10:1 v/v mixture of methylene chloride and ethyl acetate as eluent. There was thus obtained diethyl N-[5-(N-tert-butoxycarbonyl-N-methylamino)-picolinoyl]-L-glutamate (0.48 g).

A mixture of this ester and trifluoroacetic acid (10 ml) was stirred at 0° C. for 1 hour and evaporated to dryness. The residue was washed with diethyl ether and dried. There was thus obtained as a gum diethyl N-[5-(methylamino)picolinoyl]-L-glutamate (0.4 g) which was used without further purification.

Note (7): The process described in Note (6) was repeated except that methyl 5-[N-tert-butoxycarbonyl-N-(prop-2-ynyl)amino]picolinate (prepared using the method described in the Journal of Medicinal Chemistry 1980, 23, 1405, except that propargyl bromide was used in place of 3-trifluoromethylbenzyl chloride) was used in place of the corresponding methylaminopicolinate. There was thus obtained as a gum diethyl N-{5-[N-(prop-2-ynyl)amino]picolinoyl}-L-glutamate.

Note (8): The mono-sodium salt of the glutamic acid was obtained. Diethyl N-[6-(methylamino)nicotinoyl]-L-glutamate used as starting material was prepared as follows:

A mixture of 6-chloronicotinic acid (8.27 g) oxalyl chloride (5.63 ml), methylene chloride (70 ml) and dimethylformamide (0.25 ml) was stirred at laboratory temperature for 16 hours and evaporated to dryness. A solution of the residue in methylene chloride (100 ml) was added to a mixture of diethyl L-glutamate hydrochloride (13.6 g), triethylamine (22 ml) and methylene chloride (100 ml). The mixture was stirred at laboratory temperature for 16 hours, washed with water (100 ml), dried over sodium sulphate, filtered and evaporated. The residue was purified by chromatography on a silica gel column using a 4:1 v/v mixture of methylene chloride and ethyl acetate as eluent. There was thus obtained diethyl N-(6-chloronicotinoyl)-L-glutamate (17 g), as an oil.

A mixture of this product (0.53 g), N-benzyl-N-methylamine (0.49 ml) and N-methylpyrrolidin-2-one (2 ml) was stirred and heated to 100° C. for 16 hours under an atmosphere of argon. The mixture was evaporated and the residue was partitioned between ethyl acetate and a saturated aqueous sodium bicarbonate solution. The organic layer was dried over sodium sulphate, filtered and evaporated. The residue was purified by chromatography on a silica gel column using a 4:1 v/v mixture of methylene chloride and ethyl acetate as eluent. There was thus obtained diethyl N-[6-(N-benzyl-N-methylamino)nicotinoyl]-L-glutamate (0.57 g) as an oil.

A mixture of this product (0.3 g), trifluoroacetic acid (1 ml), palladium-on-charcoal catalyst (10%, 0.05 g) and ethanol (2 ml) was stirred at 60° C. for 2 hours. The mixture was filtered and the filtrate was evaporated. The residue was partitioned between ethyl acetate and a saturated aqueous sodium bicarbonate solution. The organic layer was dried over sodium sulphate, filtered and evaporated. There was thus obtained diethyl N-[6-

(methylamino)nicotinoyl]-L-glutamate (0.22 g) which was used without further purification.

EXAMPLE 8

The process described in the first paragraph of Example 3 was repeated except that 6-bromomethyl-2,4-dimethoxyquinazoline was used in place of 6-bromomethyl-3,4-dihydro-2-methylquinazolin-4-one.

A mixture of the product (1.8 g), ethanol (20 ml), aqueous N-sodium hydroxide solution (26.9 ml) and water (20 ml) was stirred at 60° C. for 16 hours. The mixture was evaporated on a rotary evaporator to a volume of approximately 10 ml, filtered and acidified to pH 3 by adding 2N-hydrochloric acid solution. The mixture was centrifuged and the solid residue was washed with water (4×30 ml) and dried. There was thus obtained N-p-[N-(3,4-dihydro-2-methoxy-4-oxoquinazolin-6-ylmethyl)-N-methylamino]benzoyl-L-glutamic acid (containing 2.5 equivalents of water; 0.55 g), m.p. 240°–245° C.

NMR Spectrum: (CD$_3$SOCD$_3$) 2.0 (m, 2H, CH$_2$), 2.32 (t, 2H, CH$_2$CO$_2$H), 3.09 (s, 3H, CH$_3$N), 3.93 (s, 3H, CH$_3$O), 4.45 (m, 1H, NHCH), 4.75 (s, 2H, CH$_2$N), 6.77 (d, 2H, aromatic, J=9 Hz), 7.44 (d, 1H, 8-H, J=9 Hz), 7.55 (d of d's, 1H, 7-H, J=2 and 9 Hz), 7.74 (d, 2H, aromatic, J=9 Hz), 7.84 (d, 1H, 5-H, J=2 Hz), 8.17 (d, 1H, NH, J=8 Hz);

Mass Spectrum: (negative ion FAB) m/e 467 (P-1)

Elemental Analysis: Found C, 53.8; H, 4.8; N, 10.7; C$_{23}$H$_{24}$N$_4$O$_7$.2.5 H$_2$O requires C, 53.8; H, 5.65; N, 10.9%.

The bromomethylquinazoline used as starting material was obtained as follows:

A mixture of 2,4-dimethoxy-6-methylquinazoline (8.2 g), N-bromosuccinimide (7.9 g), benzoyl peroxide (0.19 g) and carbon tetrachloride (200 ml) was heated to reflux for 2 hours. The warm solution was filtered and the filtrate was evaporated to give 6-bromomethyl-2,4-dimethoxyquinazoline (11.7 g), m.p. 138°–143° C.

EXAMPLE 9

The process described in Example 8 was repeated except that the appropriate diethyl or di-tert-butyl L-glutamate was used in place of diethyl N-(p-methylaminobenzoyl)-L-glutamate. There were thus obtained the compounds described in the following table, the structures of which were confirmed by proton magnetic resonance and mass spectroscopy and by elemental analysis.

TABLE III

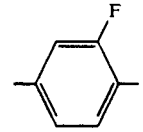

| EXAMPLE 9 Compound No | R$^2$ (Note) | Ar | x | m.p. |
| --- | --- | --- | --- | --- |
| 1 | H | 1,4-phenylene | 1 | 150–160° C. |
| 2 | ethyl | 1,4-phenylene | 1 | 140–146° C. |
| 3 | prop-2-ynyl | 1,4-phenylene | 1 | 155–165° C. |
| 4 | prop-2-enyl | 1,4-phenylene | 1 | 130–134° C. |
| 5 | 2-hydroxyethyl | 1,4-phenylene | 1.25 | 150–175° C. |
| 6 | 3-hydroxyethyl | 1,4-phenylene | 1.5 | 145–155° C. |
| 7 | 2-fluoroethyl | 1,4-phenylene | 1.25 | 141–145° C. |
| 8 | carboxymethyl (1) | 1,4-phenylene | 2 | 165–185° C. |
| 9 | 2-aminoethyl (2) | 1,4-phenylene | 0.75 | 217–220° C. |
| 10 | ethyl |  | 0.5 | 140–145° C. |
| 11 | ethyl | thien-2,5-diyl | 1.25 | 132–135° C. |

Note (1): Diethyl p-(carboethoxymethylamino)benzoyl-L-glutamate used in the preparation of this compound has been described (Journal of Medicinal Chemistry, 1985, 28, 1468).

Note (2): Di-tert-butyl N-[p-(2-phthalimidoethyl)aminobenzoyl]-L-glutamate was reacted with 6-bromomethyl-2,4-dimethoxyquinazoline using the process described in the first paragraph of Example 3. A mixture of the product (2.1 g), 3-dimethylaminopropylamine (2.12 ml), di-isopropylethylamine (0.98 ml) and methanol (18 ml) was heated to reflux for 11 hours and evaporated to dryness. The residue was purified by chromatography on a silica gel column using a 20:1 v/v mixture of methylene chloride and methanol as eluent. There was thus obtained di-tert-butyl N-p-[N-(2-aminoethyl)-N-(2,4-dimethoxyquinazolin-6-ylmethyl)amino]benzoyl-L-glutamate (0.7 g). This di-ester was hydrolysed using the conditions described in the second paragraph of Example 8 to provide N-p-[N-(2-aminoethyl)-N-(3,4-dihydro-2-methoxy-4-oxoquinazolin-6-ylmethyl)amino]benzoyl-L-glutamic acid.

The di-tert-butyl ester used as starting material was obtained as follows:

A mixture of di-tert-butyl N-(p-aminobenzoyl-L-glutamate (Journal of Medicinal Chemistry 1985, 28, 1468; 5.1 g), N-(2-bromoethyl)phthalimide (20.4 g), 2,6-lutidine (9.4 ml) and N,N-dimethylacetamide (20 ml) was heated to 100° C. for 18 hours under an atmosphere of argon. The mixture was cooled, poured into aqueous N-sulphuric acid solution (110 ml) and extracted with ethyl acetate (3×70 ml). The combined extracts were washed with a saturated aqueous sodium chloride solution (3×50 ml), dried over magnesium sulphate, filtered and evaporated. The residue was purified by chromatography on a silica gel column using a 10:1 v/v mixture of methylene chloride and ethyl acetate as eluent. There was thus obtained di-tert-butyl N-[p-(2-phthalimdioethyl)aminobenzoyl]-L-glutamate (5.3 g), m.p. 157°-158° C.

EXAMPLE 10

The process described in Example 8 was repeated using diethyl N-[p-(prop-2-ynyl)aminobenzoyl]-L-glutamate and the appropriate 2,4-dialkoxy- or 2,4-diaryloxy-6-bromomethylquinazoline. There was thus obtained the compounds described in the following table, the structures of which were confirmed by proton magentic resonance and mass spectroscopy and by elemental analysis.

TABLE IV

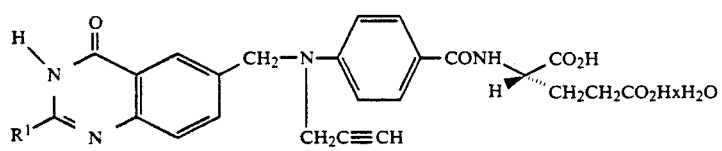

EXAMPLE 10

| Compound No | $R^1$ | (Note) | x | m.p. |
|---|---|---|---|---|
| 1 | ethoxy | (1) | 2 | 134–136° C. |
| 2 | 2-methoxyethoxy | (2) | 1 | 134–140° C. |
| 3 | 2-hydroxyethoxy | (3) | 2 | 145–149° C. |
| 4 | phenoxy | (4) | 3 | 159–164° C. |

Note (1): The bromomethyl compound used as starting material was obtained as follows:

A mixture of 2.4-dichloro-6-methylquinazoline (3 g) and a solution of sodium ethoxide [made by adding sodium metal (1.07 g) to ethanol (100 ml)] was heated to reflux for 4 hours, cooled, poured into a saturated aqueous sodium chloride solution (100 ml) and extracted with ethyl acetate (3×90 ml). The combined extracts were washed with water, dried over magnesium sulphate, filtered and evaporated to dryness. The residue was purified by chromatography on a silica gel column using a 10:1 v/v mixture of methylene chloride and ethyl acetate as eluent. There was thus obtained 2,4-diethoxy-6-methylquinazoline (1.9 g), m.p. 60°-62° C., which was converted to the 6-bromomethyl derivative using the process described in the last paragraph of Example 8.

Note (2): The bromomethyl compound used as starting material was obtained using the process described above, starting from 2,4-dichloro-6-methylquinazoline but using the sodium salt of 2-methoxyethanol instead of sodium ethoxide.

Note (3): The bromomethyl compound used as starting material was obtained as follows:

Ethylene glycol (30 ml) was added to sodium hydride (2.4 g of a 50% dispersion in oil which was washed with hexane under an atmosphere of argon). A solution of 2,4-dichloro-6-methylquinazoline (2.06 g) in dimethylformamide (5 ml) was added and the mixture was stirred at 100° C. for 16 hours, cooled, poured onto water (100 ml) and extracted with ethyl acetate (3×200 ml). The combined extracts were washed with a saturated aqeous sodium chloride solution, dried over magnesium sulphate, filtered and evaporated. A mixture of the product (2 g), anhydrous pyridine (20 ml) and benzoyl chloride (1.9 ml) was stirred at laboratory temperature for 16 hours, poured into water (100 ml) and extracted with methylene chloride (3×70 ml). The combined extracts were washed with a saturated aqueous sodium bicarbonate solution (100 ml) and with water (50 ml), dried over magnesium sulphate, filtered and evaporated. The residue was purified by chromatography on a silica gel column using a 20:1 v/v mixture of methylene chloride and ethyl acetate as eluent. There was thus obtained 2,4-di-(2-benzoyloxyethoxy)-6-methylquinazoline (1.3 g) which was converted to the 6-bromomethyl derivative using the process described in the last paragraph of Example 8.

The process described in Example 8 was then repeated and the final aqueous basic hydrolysis was used to removed the benzoyl protecting groups.

Note (4): The bromomethyl compound used as starting material was obtained as follows:

A mixture of a solution of sodium phenoxide in molten phenol (obtained on the addition of sodium metal (0.8 g) to molten phenol (30 g) at 80° C.) and 2,4-dichloro-6-methylquinazoline (3.2 g) was heated to 180° C. for 1 hour. The warm mixture was poured into water (200 ml), an aqueous 10N-sodium hydroxide solution (5 ml) was added followed by glacial acetic acid to bring the acidity of the mixture to pH 6. The solid was filtered off, washed with water, dissolved in methylene chloride and dried over magnesium sulphate. The solution was passed through a silica gel column using more methylene chloride as eluent. There was thus obtained 2,4-diphenoxy-6-methylquinazoline (4.6 g), m.p. 184°-185° C., which was converted to the 6-bromomethyl derivative using the process described in the last paragraph of Example 8.

EXAMPLE 11

Diphenylphosphoryl azide (0.44 g) and triethylamine (0.67 ml) were added successively to a mixture of p-[N-(3,4-dihydro-2-methyl-4-oxoquinazolin-6-ylmethyl)-N-(prop-2-ynyl)amino]benzoic acid (as its trifluoroacetic acid salt; 0.5 g), L-alanine ethyl ester (as its hydrochloride salt; 0.27 g) and dimethylformamide (20 ml) which was cooled in an ice-bath to 0° C. The mixture was stirred at 0° C. for 5 hours and at laboratory temperature for 48 hours, poured into a mixture of ice and water (100 ml) and centrifuged. The solid residue was washed with water (3×10 ml) and dried. The residue was purified by chromatography on a silica column using a 24:1 v/v mixture of methylene chloride and ethanol as eluent.

A mixture of the product (0.11 g), ethanol (4 ml), water (4 ml) and aqueous N-sodium hydroxide solution (0.64 ml) was stirred at laboratory temperature for 2 hours, acidified to pH 3 with aqueous 0.2N-hydrochloric acid solution and centrifuged. The solid residue was washed with water (5×10 ml) and dried. There was thus obtained N-p-[N-(3,4-dihydro-2-methyl-4-oxoquinazolin-6-ylmethyl)-N-(prop-2-ynyl)amino]benzoyl-L-alanine (0.08 g), as a monohydrate, m.p 165°-170° C.

NMR Spectrum: (CD$_3$SOCD$_3$) 1.32 (d, 3H, CH$_3$; J=7 Hz), 2.31 (s, 3H, CH$_3$), 3.18 (t,1H, C≡CH, J=2 Hz), 4.3 (m, 3H, NHCH and CH$_2$C≡CH), 4.78 (s, 2H, CH$_2$N), 6.83 (d, 2H, aromatic, J=9 Hz), 7.52 (d, 1H, 8-H, J=8.5 Hz), 7.68 (d of d's, 1H, 7-H, J=2 and 8.5 Hz), 7.72 (d, 2H, aromatic, J=9 Hz), 7.96 (d, 1H, 5-H, J=2Hz), 8.21 (d, 1H, NH, J=6.5 Hz), 12.13 (s, 1H, NH);

Mass Spectrum: (negative ion FAB) m/e 418 (P-1); Elemental Analysis: Found C, 63.0; H, 5.3; N, 12.3; C$_{23}$H$_{22}$N$_4$O$_4$.H$_2$O requires C, 63.3; H, 5.5; N, 12.8%.

The process described in Example 11 was repeated using L-phenylalanine ethyl ester, L-serine methyl ester and L-aspartic acid dimethyl ester respectively in place of alanine ethyl ester. There were thus obtained N-p-[N-(3,4-dihydro-2-methyl-4-oxoquinazolin-6-ylmethyl)-N-(prop-2-ynyl)amino]benzoyl-L-phenylalanine as a monohydrate, m.p 152°-155° C., the corresponding benzoyl-L-serine, as a hemi-hydrate m.p. 200°-204° C., and the corresponding benzoyl-L-aspartic acid (containing 1.25 equivalents of water), m.p. 180°-190° C. (decomposes).

The process described in the first paragraph of Example 11 was also repeated using N$^5$-benzyloxycarbonyl-L-ornithine tert-butyl ester in place of alanine ethyl ester.

Boron tris(trifluoroacetate) (1 ml of a 1 molar solution in trifluoroacetic acid) was added to a solution of the product (0.1 g) in trifluoroacetic acid (1 ml) which had been cooled to −10° C. The mixture was stirred at 50° C. for 3 hours, methanol (2 ml) was added and the mixture was evaporated. The residue was purified by chromatography on a preparative thin-layer chromatography plate using a 4:1 v/v mixture of ethanol and an aqueous ammonia solution (concentrated) as solvent. There was thus obtained N-p-[N-(3,4-dihydro-2-methyl-4-oxoquinazolin-6-ylmethyl)-N-(prop-2-ynyl)amino]-benzoyl-L-ornithine, as a monohydrate (15 mg), m.p. 210°-215° C. (decomposes).

N-p-[N-(3,4-Dihydro-2-methyl-4-oxoquinazolin-6-ylmethyl)-N-(prop-2-ynyl)amino]benzoic acid used as starting material was obtained as follows:

A mixture of tert-butyl p-aminobenzoate (Synth. Commun., 1984, 14, 921; 10.5 g), propargyl bromide (7.3 ml of an 80% solution in toluene), potassium carbonate (7.5 g) and N,N-dimethylacetamide (85 ml) was heated to 50° C. for 24 hours, cooled, filtered and evaporated. The residue was purified by chromatography on a silica gel column using a 6:1 v/v mixture of hexane and and ethyl acetate as eluent.

A mixture of the product (7.3 g), 6-bromomethyl-3,4-dihydro-2-methylquinazolin-4-one (prepared as described in Example 3 above; 8 g), calcium carbonate (3.2 g) and dimethylformamide (100 ml) was stirred at laboratory temperature for 65 hours, filtered and evaporated. The residue was purified by chromatography on a silica gel column using ethyl acetate as eluent.

The mixture of the product (2.5 g) and trifluoroacetic acid (25 ml) was stirred at laboratory temperature for 10 minutes and evaporated to give the p-aminobenzoic acid as its trifluoroacetic acid salt (2.5 g).

EXAMPLE 12

A mixture of 6-bromomethyl-3,4-dihydro-2-methylquinazolin-4-one (1.24 g), methyl N-[p-(prop-2-ynyl)aminobenzoyl]glycine (prepared as described in the Journal of Medicinal Chemistry, 1986, 29, 1117; 1.2 g), calcium carbonate (0.5 g) and dimethylformamide (12 ml) was stirred at laboratory temperature for 72 hours, filtered and evaporated. The residue was purified by chromatography on a column of silica gel using a 9:1 v/v mixture of ethyl acetate and methanol as eluent.

A portion of the product (0.17 g) was hydrolysed under basic conditions using the process described in the second paragraph of Example 11. There was thus obtained N-p-[N-(3,4-dihydro-2-methyl-4-oxoquinazolin-6-ylmethyl)-N-(prop-2-ynyl)amino]benzoylglycine (0.09 g; containing 1.5 equivalents of water) m.p. 240°-250° C. (decomposes).

EXAMPLE 13

The process described in the second paragraph of Example 3 was repeated except that diethyl N-p-[N-(3,4-dihydro-2-methylthio-4-oxoquinazolin-6-ylmethyl)-N-(prop-2-ynyl)amino]benzoyl-L-glutamate was used as starting material. There was thus obtained N-p-[N-(3,4-dihydro-2-methylthio-4-oxoquinazolin-6-ylmethyl)-N-(prop-2-ynyl)amino]benzoyl-L-glutamic acid (containing 0.75 equivalents of water), m.p. 157°-163° C.

The starting material was obtained as follows:

A mixture of diethyl N-p-[N-(2-chloro-3,4-dihydro-4-oxoquinazolin-6-ylmethyl)-N-(prop-2-ynyl)amino]benzoyl-L-glutamate (obtained using the process described in Example 4; 0.75 g), thiourea (0.125 g), formic acid (0.05 ml) and ethanol (20 ml) was heated to reflux for 15 minutes, cooled and evaporated to dryness. The residue was purified by chromatography on a silica gel column using a 10:3 v/v mixture of methylene chloride and ethyl acetate as eluent. There was thus obtained diethyl N-p-[N-(4-oxo-1,2,3,4-tetrahydro-2-thioxoquinazolin-6-ylmethyl)-N-(prop-2-ynyl)amino]benzoyl-L-glutamate, m.p. 92°-94° C.

A mixture of this product (0.19 g), water (12.8 ml), ethanol (9.5 ml) and an aqueous ammonia solution (3.2 ml of a solution of specific gravity of 0.88 g ml$^{-1}$) was stirred at laboratory temperature for 10 minutes. Methyl iodide (0.13 ml) was added and the mixture was stirred for 1 hour. The precipitated solid was filtered off, washed with a 1:1 v/v mixture of water and ethanol and dried. There was thus obtained diethyl N-p-[N-(3,4-dihydro-2-methylthio-4-oxoquinazolin-6-ylmethyl)-N-(prop-2-ynyl)amino]benzoyl-L-glutamate (0.16 g; containing 0.75 equivalents of water), m.p. 230°-233° C.

Alternatively the product described in the first paragraph above concerned with the production of starting materials may be hydrolysed with base using the process described in the second paragraph of Example 3. There was thus obtained N-p-[N-(4-oxo-1,2,3,4-tetrahydro-2-thioxoquinazolin-6-ylmethyl)-N-(prop-2-ynyl)amino]benzoyl-L-glutamic acid as a monohydrate, m.p. 161°-166° C.

EXAMPLE 14

The process described in the second paragraph of Example 3 was repeated except that diethyl N-p-{N-[3,4-dihydro-4-oxo-2-(pyrimidin-2-ylthio)quinazolin-6-ylmethyl]-N-(prop-2-ynyl)amino}benzoyl-L-glutamate was used as starting material. There was thus obtained N-p-{N-[3,4-dihydro-4-oxo-2-(pyrimidin-2-ylthio)-quinazolin-6-ylmethyl]-N-(prop-2-ynyl)amino}benzoyl-L-glutamic acid (containing 0.5 equivalents of water), m.p. 143°–147° C.

The diethyl p-aminobenzoyl-L-glutamate used as starting material was obtained as follows:

A mixture of diethyl N-p-[N-(2-chloro-3,4-dihydro-4-oxoquinazolin-6-ylmethyl)-N-(prop-2-ynyl)amino]benzoyl-L-glutamate (obtained using the process described in Example 4; 0.35 g), 2-mercaptopyrimidine (0.21 g) and N-methylpyrrolid-2-one (5 ml) was stirred at laboratory temperature for 16 hours, poured into water (20 ml) and extracted with ethyl acetate (3×20 ml). The combined extracts were washed with water, dried over magnesium sulphate, filtered and evaporated. The residue was purified by chromatography on a silica gel column using a 3:2 v/v mixture of methylene chloride and ethyl acetate as eluent. There was thus obtained diethyl N-p-{N-[3,4-dihydro-4-oxo-2-(pyrimidin-2-ylthio)quinazolin-6-ylmethyl]-N-(prop-2-ynyl)amino} benzoyl-L-glutamate (0.19 g), as a monohydrate, m.p. 163°–165° C.

EXAMPLE 15

A mixture of diethyl N-p-[N-2-chloromethyl-3,4-dihydro-4-oxoquinazolin-6-ylmethyl)-N-(prop-2-ynyl)amino]benzoyl-L-glutamate (0.56 g), 2-mercaptopyrimidine (0.11 g), sodium hydride (0.047 g of a 50% dispersion in oil which was washed with hexane) and dimethylformamide (10 ml) was stirred at laboratory temperature for 16 hours, poured into water (50 ml) and extracted with ethyl acetate (4×25 ml). The combined extracts were washed with water (2×25 ml), dried over magnesium sulphate, filtered and evaporated. The residue was purified by chromatography on a column of silica gel using ethyl acetate as eluent.

The product was hydrolysed with base using the process described in the second paragraph of Example 3. There was thus obtained N-p-{N-[3,4-dihydro-4-oxo-2-(pyrimidin-2-ylthiomethyl)quinazolin-6-ylmethyl]-N-(prop-2-ynyl)amino}benzoyl-L-glutamic acid (0.32 g; containing 1.5 equivalents of water), m.p. 151°–153° C.

The diethyl L-glutamate used as starting material was obtained as follows:

The process described in the paragraph in Example 3 which is concerned with the preparation of starting materials was repeated except that 2-chloromethyl-3,4-dihydro-6-methylquinazolin-4-one (Dissertationes Pharmaceuticae et Pharmacologicae 1968, 20, 29) was used in place of 3,4-dihydro-2,6-dimethylquinazolin-4-one. There was thus obtained 6-bromomethyl-2-chloromethyl-3,4-dihydroquinazolin-4-one.

The process described in the first paragraph of Example 3 was repeated except that the 6-bromomethyl-2-chloromethyl-3,4-dihydroquinazolin-4-one and diethyl N-p-(prop-2-ynyl)aminobenzoyl-L-glutamate were used as starting materials. There was thus obtained diethyl N-p-[N-(2-chloromethyl-3,4-dihydro-4-oxoquinazolin-6-ylmethyl)-N-(prop-2-ynyl)amino]benzoyl-L-glutamate.

EXAMPLE 16

A mixture of 6-bromomethyl-3,4-dihydro-2-methylquinazolin-4-one (5.1 g), diethyl N-p-(prop-2-ynyl)amino-o-trifluoromethylbenzoyl-L-glutamate (1.1 g), magnesium oxide (0.12 g) and N,N-dimethylacetamide (30 ml) was stirred and heated to 80° C. for 19 hours. The mixture was cooled, poured onto ice (100 ml) and extracted with ethyl acetate (3×200 ml). The combined extracts were washed with water (2×100 ml), dried over sodium sulphate, filtered and evaporated. The residue was purified by chromatography on a silica gel column using a 50:1 v/v mixture of methylene chloride and methanol as eluent. There was thus obtained diethyl N-p-[N-(3,4-dihydro-2-methyl-4-oxoquinazolin-6-ylmethyl)-N-(prop-2-ynyl)amino]-o-trifluoromethylbenzoyl-L-glutamate (0.96 g), m.p. 191° C.

A mixture of a portion of this product (0.49 g), ethanol (15 ml), water (15 ml) and aqueous N-sodium hydroxide solution (2.5 ml) was stirred at laboratory temperature for 17 hours. The mixture was filtered and the filtrate was acidified to pH 4 by adding N-hydrochloric acid solution. The mixture was centrifuged and the solid residue was washed three times with water and dried. There was thus obtained N-p-[N-(3,4-dihydro-2-methyl-4-oxoquinazolin-6-ylmethyl)-N-(prop-2-ynyl)amino]-o-trifluoromethylbenzoyl-L-glutamic acid (0.38 g, as hemihydrate), m.p. 197° C.

The diethyl glutamate used as starting material was obtained as follows:

A mixture of 4-nitro-2-trifluoromethylbenzonitrile (J. Amer. Chem. Soc. 1954, 76, 1051; 5.6 g), glacial acetic acid (20 ml) and sulphuric acid (concentrated, 30 ml) was stirred and heated to 130° C. for 45 minutes. The mixture was cooled, poured onto ice (100 ml) and extracted with ethyl acetate (3×150 ml). The combined extracts were washed with aqueous 0.05N-hydrochloric acid solution, dried over sodium sulphate, filtered and evaporated. The residue was purified by chromatography on a silica gel column using ethyl acetate as eluent. There was thus obtained 4-nitro-2-trifluoromethylbenzamide (5.16 g), m.p. 192° C.

A mixture of this product (1.82 g), water (50 ml), sodium hydroxide (2 g) and hydrogen peroxide (30%, 10 ml) was stirred and heated to 70° C. for 4 hours during which time one further portion of sodium hydroxide (2 g) and two further portions of hydrogen peroxide (30%, 10 ml each time) were added. The mixture was heated to 70° C. for 3 days, cooled, acidified with aqueous N-hydrochloric acid solution and extracted with ethyl acetate (3×100 ml). The combined extracts were washed with aqueous 0.05N-hydrochloric acid solution, dried over sodium sulphate, filtered and evaporated to leave, as a light brown solid, 4-nitro-2-trifluoromethylbenzoic acid (1.76 g), m.p. 128°–129° C. (J. Amer. Chem. Soc., 1954, 76, 1051; m.p. 137°–140° C.).

A mixture of this product (0.79 g), toluene (50 ml) and thionyl chloride (2 ml) was heated to reflux for 5 hours, cooled and evaporated. A solution of the residue in methylene chloride (50 ml) was added to a stirred mixture of diethyl L-glutamate hydrochloride (0.68 g), triethylamine (0.75 g) and methylene chloride (100 ml) which was cooled to 4° C. The mixture was stirred at laboratory temperature for 2 hours, washed with water (4×100 ml), dried over sodium sulphate, filtered and evaporated. The residue was purified by chromatography on a silica gel column using a 9:1 v/v mixture of methylene chloride and ethyl acetate as eluent. There was thus obtained diethyl N-p-nitro-o-trifluoromethylbenzoyl-L-glutamate (1.23 g) m.p. 105° C. (recrystallised from ethanol solution).

After repetition of the above reactions on a larger scale a mixture of this product (12.5 g), ethanol (1 liter) and palladium-on-charcoal catalyst (10%, 1 g) was stirred under an atmosphere of hydrogen until the calculated volume of hydrogen had been consumed. The mixture was filtered and evaporated to leave an oil which crystallised on standing. There was thus obtained diethyl N-p-amino-o-trifluoromethylbenzoyl-L-glutamate (11.6 g), m.p. 95° C.

A mixture of this product (10.2 g), propargyl bromide (as an 80% solution in toluene, 8.5 g), potassium carbonate (7.2 g) and dry dimethylformamide (150 ml) was stirred and heated to 100° C. for 100 minutes. The mixture was cooled, poured onto ice (100 ml) and extracted with ethyl acetate (3×200 ml). The combined extracts were washed with water (2×200 ml), dried over sodium sulphate, filtered and evaporated. The residue was purified by chromatography on a silica gel column using a 2:1 v/v mixture of petroleum ether (b.p. 60°-80° C.) and ethyl acetate as eluent. There was thus obtained diethyl N-p-(prop-2-ynyl)amino-o-trifluoromethylbenzoyl-L-glutamate (7.3 g), m.p. 91° C.

EXAMPLE 17

The process described in Example 3 was repeated using 6-bromomethyl-3,4-dihydro-2-methylquinazolin-4-one (prepared as described in Example 3) as the appropriate quinazolinone; the appropriate diethyl L-glutamate and the appropriate organic or inorganic base in the first step. There were thus obtained the compounds described in the following table, the structures of which were confirmed by proton magnetic resonance and mass spectroscopy and by elemental analysis.

TABLE V

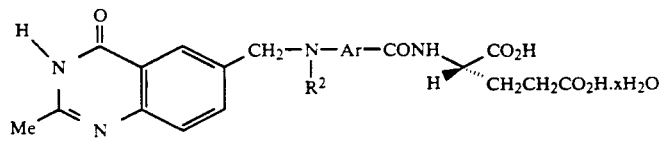

| Example 17 Compound No. | R² | Note | Ar | x | m.p. |
|---|---|---|---|---|---|
| 1 | ethyl | (1) | OMe (phenyl) | 1 | 152–157° C. |
| 2 | prop-2-ynyl | (2) | OMe (phenyl) | 2.5 | 175–180° C. |
| 3 | ethyl | (3) | NHCOMe (phenyl) | 1 | 211° C. (dec) |
| 4 | prop-2-ynyl | (4) | F (phenyl) | 1 | 156–160° C. |
| 5 | prop-2-ynyl | (5) | OH (phenyl) | 1 | 210° C. (dec) |
| 6 | ethyl | (6) | Cl (phenyl) | 1 | 201–207° C. |

TABLE V-continued

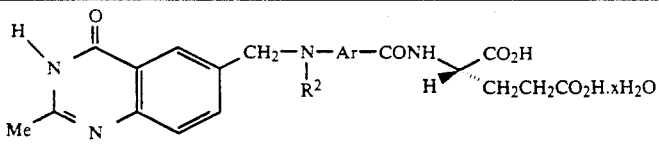

Example 17
Compound

| No. | R² | Note | Ar | x | m.p. |
|---|---|---|---|---|---|
| 7 | prop-2-ynyl | (6) | Cl (2,4-disubstituted phenyl) | 0.5 | 162–164° C. |

Note (1): Diethyl N (4-ethylamino-2-methoxybenzoyl)-L-glutamate was obtained using the process described in the last three paragraphs of the portion of Example 16 which is concerned with the preparation of starting materials except that 2-methoxy-4-nitrobenzoic acid (Journal of the Chemical Society, 1917, 111, 232) was used in place of 4-nitro-2-trifluoromethylbenzoic acid and ethyl iodide was used in place of propargyl bromide.

Note (2): Diethyl N-[2-methoxy-4-(prop-2-ynyl)aminobenzoyl]-L-glutamate was obtained using the process described in the last three paragraphs of the portion of Example 16 which is concerned with the preparation of starting materials except that 2-methoxy-4-nitrobenzoic acid (Journal of the Chemical Society, 1917, 111, 232) was used in place of 4-nitro-2-trifluoromethylbenzoic acid.

Note (3): Diethyl N-(2-acetamido-4-ethylaminobenzoyl)-L-glutamate was obtained using the process described in the last three paragraphs of the portion of Example 16 which is concerned with the preparation of starting materials except that 2-acetamido-4-nitrobenzoic acid (Journal of the Chemical Society, 1925, 127, 1795, was used in place of 4-nitro-2-trifluoromethylbenzoic acid and ethyl iodide was used in place of propargyl bromide.

Note (4) Naphthalene-1,8-diamine was used as the base in place of 2,6-lutidine. Diethyl N-[3-fluoro-4-(prop-2-ynyl)aminobenzoyl]-L-glutamate was obtained using the process described in the last three paragraphs of the portion of Example 16 which is concerned with the preparation of starting materials except that 3-fluoro-4-nitrobenzoic acid (Journal of the American Chemical Society, 1944, 66, 1631) was used in place of 4-nitro-3-trifluoromethylbenzoic acid.

Note (5): Diethyl N-[2-acetoxy-4-(prop-2-ynyl)aminobenzoyl] L-glutamate was obtained using the process described in the last three paragraphs of the portion of Example 16 which is concerned with the preparation of starting materials except that 2-acetoxy-4-nitrobenzoic acid [obtained by the reaction of 2-hydroxy-4-nitrobenzoic acid (The Dictionary of Organic Compounds, Volume 3, page 3169; Chapman and Hall, 1982) and acetic anhydride at laboratory temperature] was used in place of 4-nitro-3-trifluorobenzoic acid.

The conditions of the last step of the process described in Example 3, that is, the hydrolysis under basic conditions of the appropriate diethyl glutamate, resulted in the hydrolysis of the 2-acetoxy group. There was thus obtained N-p-[N-(3,4-dihydro-2-methyl-4-oxoquinazolin-6-ylmethyl)-N-(prop-2-ynyl)amino]-o-hydroxybenzoyl-L-glutamic acid.

Note (6): Diethyl N-[2-chloro-4-(prop-2-ynyl)aminobenzoyl]-L-glutamate was prepared from diethyl N-(4-amino-2-chlorobenzoyl)-L-glutamate (Journal of Medicinal Chemistry, 1986, 29, 468). The corresponding 4-ethylaminobenzoyl-L-glutamate was prepared from the 4-amino derivative using the method described in the European Journal of Cancer, 1981, 17, 11.

EXAMPLE 18

A mixture of p-[N-(3,4-dihydro-2-methyl-4-oxoquinazolin-6-ylmethyl)-N-ethylamino]-o-nitrobenzoic acid (2.5 g), oxalyl chloride (0.93 g), tetrahydrofuran (200 ml) and dimethylformamide (1 drop) was stirred at laboratory temperature for 18 hours and evaporated. A solution of the residue in tetrahydrofuran (200 ml) was added to a stirred mixture of diethyl L-glutamate hydrochloride (1.77 g), triethylamine (10 ml) and tetrahydrofuran (25 ml). The mixture was stirred at laboratory temperature for 2 hours, washed with water (2×50 ml), with a saturated aqueous sodium chloride solution (50 ml), dried over magnesium sulphate, filtered and evaporated. The residue was purified by chromatography on a silica gel column using a 10:1 v/v mixture of ethyl acetate and methanol as eluent. There was thus obtained diethyl N-p-[N-(3,4-dihydro-2-methyl-4-oxoquinazolin-6-ylmethyl)-N-ethylamino]-o-nitrobenzoyl-L-glutamate (0.64 g).

A mixture of this product (0.64 g) and an aqueous N-sodium hydroxide solution (10 ml) was stirred at laboratory temperature for 2 hours then acidified to pH 4 by the addition of an aqueous 2N-hydrochloric acid solution. The mixture was centrifuged and the solid residue was washed with water (4×10 ml) and acetone (10 ml) and dried. There was thus obtained N-p-[N-(3,4-dihydro-2-methyl-4-oxoquinazolin-6-ylmethyl)-N-ethylamino]-o-nitrobenzoyl-L-glutamic acid as a monohydrate (0.13 g), m.p. 192°–200° C. (decomposes)

The benzoic acid used as starting material was obtained as follows:

A mixture of methyl-p-amino-o-nitrobenzoate (The Dictionary of Organic Compuonds, Volume 1, page 285; Chapman and Hall, 1982; 1 g), ethyl iodide (0.8 g), 2,6-lutidine (2.7 g) and dimethylformamide (5 ml) was stirred and heated to 80° C. for 18 hours, cooled and evaporated. A mixture of the residue, 2,6-lutidine (2.7 g), 6-bromomethyl-3,4-dihydro-2-methylquinazolin-4-one (1.3 g) and dimethylformamide (10 ml) was stirred at 85° C. for 5 hours, cooled, poured into water (100 ml) and extracted with ethyl acetate (3×70 ml).

The combined extracts were washed with a saturated aqueous sodium chloride solution (70 ml), dried over magnesium sulphate, filtered and evaporated. The residue was purified by chromatography on a silica gel column using a 50:1 v/v mixture of ethyl acetate and methanol as eluent. There was thus obtained methyl p-[N-(3,4-dihydro-2-methyl-4-oxoquinazolin-6-ylmethyl)-N-ethylamino]-o-nitrobenzoate (0.35 g).

A mixture of this product (0.35 g) and aqueous N-sodium hydroxide solution (10 ml) was stirred at laboratory temperature for 4 hours. The mixture was acidified to pH 4 by the addition of aqueous 2N-hydrochloric acid solution. The precipitated solid was separated by filtration and dried. There was thus obtained p-[N-(3,4-dihydro-2-methyl-4-oxoquinazolin-6-ylmethyl)-N-ethylamino]-o-nitrobenzoic acid (0.3 g).

EXAMPLE 19

The process described in Example 3 was repeated using 2-acetoxymethyl-6-bromomethyl-3,4-dihydroquinazolin-4-one (prepared from the 6-methyl compound, which is described in note (5) of Example 4, using the process described in the portion of Example 3 concerned with the preparation of starting materials) in place of 6-bromomethyl-3,4-dihydro-2-methylquinazolin-4-one and, in turn, diethyl N-(5-methylamino-2-thenoyl)-L-glutamate and diethyl N-(5-ethylamino-2-thenoyl)-L-glutamate (both of which were prepared as described in note (5) of Example 7) in place of diethyl N-(p-methylaminobenzoyl)-L-glutamate. There were thus obtained N-5-[N-(3,4-dihydro-2-hydroxymethyl-4-oxo-quinazolin-6-ylmethyl)-N-methylamino]-2-thenoyl-L-glutamic acid, as its monohydrate, m.p. 180°–190° C. and N-{5-[N-(3,4-dihydro-2-hydroxymethyl-4-oxoquinazolin-6-ylmethyl)-N-ethylamino]-2-thenoyl}-L-glutamic acid, as its monohydrate, m.p. 148°–153° C.

EXAMPLE 20

The process described in Example 11 was repeated except that 2-[N-(3,4-dihydro-2-methyl-4-oxoquinazolin-6-ylmethyl)-N-ethylamino]thiazole-5-carboxylic acid was used in place of the benzoic acid and diethyl L-glutamate, as its hydrochloride salt, was used in place of L-alanine ethyl ester. There was thus obtained N-2-[N-(3,4-dihydro-2-methyl-4-oxoquinazolin-6-ylmethyl)-N-ethylamino]thiazole-5-carbonyl-L-glutamic acid as its hemi-hydrate, m.p. 160°–170° C.

The thiazole-5-carboxylic acid used as starting material was obtained as follows:

A mixture of 6-bromomethyl-3,4-dihydro-2-methylquinazolin-4-one (prepared as described in Example 3; 10 g), anhydrous ethylamine (7.9 ml) and acetonitrile (250 ml) was stirred rapidly at laboratory temperature for 4 hours. The mixture was evaporated to dryness, the residue was dissolved in water, filtered and the filtrate was evaporated. The residue was triturated in acetone to give N-(3,4-dihydro-2-methyl-4-oxoquinazolin-6-ylmethyl)-N-ethylamine, as its hydrobromide salt (8.5 g), m.p. >260° C.

A mixture of this product (6.1 g), benzoyl isothiocyanate (2.75 ml) and acetone (25 ml) was stirred and heated to 50° C. for 2 hours. The mixture was poured into water (250 ml) and the product was filtered off and dried. A mixture of this solid, aqueous hydrochloric acid (concentrated, 80 ml) and isopropanol (48 ml) was stirred and heated to 100° C. for 30 minutes. The mixture was evaporated and the residue was triturated in ethyl acetate to give N-(3,4-dihydro-2-methyl-4-oxoquinazolin-6-ylmethyl)-N-ethylthiourea (5.3 g), m.p. 186°–187° C.

A mixture of the thiourea (4.67 g), ethyl formylchloroacetate (Archiv der Pharmazie, 1953, 286, 494; 2.55 g) and dimethylformamide (25 ml) was stirred and heated to 100° C. for 1 hours. The mixture was cooled, filtered and the filtrate was evaporated. The residue was partitioned between methylene chloride and a saturated aqueous sodium bicarbonate solution. The organic solution was dried over sodium sulphate, filtered and evaporated. The residue was purified by trituration in ethyl acetate to give ethyl 2-[N-(3,4-dihydro-2-methyl-4-oxoquinazolin-6-ylmethyl)-N-ethylamino]thiazole-5-carboxylate (1.37 g), m.p. 188°–192° C.

A mixture of this ester (1.3 g) and an aqueous N-sodium hydroxide solution (10.5 ml) was heated to 48° C. for 1 hour. The mixture was cooled and acidified to pH 4 by the addition of an aqueous 2N-hydrochloric acid solution. The gummy precipitate was isolated by centrifugation and triturated in water to give the thiazole-5-carboxylic acid (1.05 g) used as starting material above.

EXAMPLE 21

The process described in Example 3 was repeated except that 6-bromomethyl-1,2,3,4-tetrahydroquinazolin-2,4-dione was used in place of 6-bromomethyl-3,4-dihydro-2-methylquinazolin-4-one and diethyl N-(p-ethylaminobenzoyl)-L-glutamate was used in place of the p-methylaminobenzoyl derivative. There was thus obtianed N-p-[N-ethyl-N-(1,2,3,4-tetrahydro-2,4-dioxoquinazolin-6-ylmethyl)amino]benzoyl-L-glutamic acid as a hemi-hydrate, m.p. 205°–211° C.

The 6-bromomethyl-1,2,3,4-tetrahydroquinazolin-2,4-dione used as starting material was obtained from 1,2,3,4-tetrahydro-6-methylquinazolin-2,4-dione (Journal of Heterocyclic Chemistry, 1984, 21, 5) using the method described in the second paragraph of the portion of Example 5 which is concerned with the preparation of starting materials.

What we claim is:

1. A pharmaceutical composition suitable for use in producing an anti-tumor effect comprising an effective amount of a quinazoline of the formula:

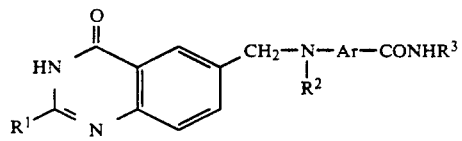

wherein $R^1$ is alkyl, cycloalkyl, alkenyl, alkynyl, alkoxy or alkylthio each of up to 6 carbon atoms; aryl, aryloxy or arylalkyl each of up to 10 carbon atoms; halogeno, hydroxy, mercapto, pyridylthio or pyrimidinylthio; alkyl of up to 3 carbon atoms which bears one, two or three halogeno substituents or which bears one or two substituents selected from hydroxy, amino, pyridylthio, pyrimidinylthio, alkoxy, alkanoyloxy, alkylthio, alkylamino, dialkylamino and alkanoylamino each of up to 6 carbon atoms and aroyloxy and aroylamino each of up to 10 carbon atoms; or alkoxy of up to 3 carbon atoms which bears one or two substituents selected from hydroxy and alkoxy of up to 6 carbon atoms;

wherein $R^2$ is hydrogen, alkyl, alkenyl, alkynyl, hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl or alkanoyl each of up to 6 carbon atoms or aroylalkyl of up to 10 carbon atoms;

wherein Ar is phenylene, naphthylene or heterocyclene which is unsubstituted or which bears one or two substituents selected from halogeno, phenyl, cyano, nitro, hydroxy, amino and carbamoyl and alkyl, alkoxy, halogenoalkyl, alkanoylamino, alkylthio and alkoxycarbonyl each of up to 6 carbon atoms; and wherein $R^3$ is such that $R^3$—$NH_2$ is L-aspartic acid, L-glutamic acid, L-alanine, L-phenylalanine, L-serine, glycine, L-ornithine, L-2-aminobutyric acid or a poly-L-glutamic acid of the formula

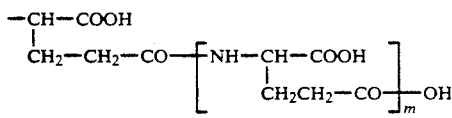

wherein m is an integer from 1 to 10; or a pharmaceutically acceptable salt or ester thereof,
together with a pharmaceutically acceptable diluent or carrier.

2. The pharmaceutical composition as claimed in claim 1, further comprising at least one other anti-tumor substance selected from mitotic inhibitors, alkylating agents, antimetabolites, intercalating antibiotics, enzymes, topoisomerase inhibitors and biological response modifiers.

3. A pharmaceutical composition as claimed in claim 1
wherein $R^1$ is methyl, ethyl, prop-2-enyl, prop-2-ynyl, methoxy, methylthio, phenyl, benzyl, fluoromethyl, difluoromethyl, trifluoromethyl, hydroxymethyl, aminomethyl, methoxymethyl, acetoxymethyl, methylthiomethyl, methylaminomethyl, dimethylaminomethyl or acetamidomethyl;
wherein $R^2$ is hydrogen, methyl, ethyl, propyl, prop-2-enyl, prop-2-ynyl, 2-hydroxyethyl, 2-methoxyethyl, 2-mercaptoethyl, 2-methylthioethyl, 2-aminoethyl, 2-methylaminoethyl, 2-dimethylaminoethyl, 2-bromoethyl or acetyl;
wherein Ar is 1,4-phenylene or thien-2,5-diyl which is unsubstituted or which bears one substituent selected from chloro, methyl, methoxy or trifluoromethyl and wherein $R^3$ is such that $R^3$—$NH_2$ is L-alanine, L-glutamic acid or L-aspartic acid.

4. A pharmaceutical composition as claimed in claim 1
wherein $R^1$ is methyl, ethyl, isopropyl, cyclopropyl, cyclohexyl, methoxy, ethoxy, phenoxy, fluoro, chloro, hydroxy, mercapto, pyrimidin-2-ylthio, pyrimidin-2-ylthiomethyl, 2-hydroxyethoxy or 2-methoxyethoxy;
wherein $R^2$ is hydrogen, methyl, ethyl, prop-2-ynyl, 3-hydroxypropyl, 3-methoxypropyl, 2-fluoroethyl, cyanomethyl, acetonyl, carboxymethyl or carbamoylmethyl;
wherein Ar is 1,4-phenylene, thien-2,5-diyl, pyrid-2,5-diyl, pyrimidin-2,5-diyl, thiazol-2,5-diyl or oxazol-2,5-diyl which is unsubstituted or which bears one substituent selected from fluoro, chloro, cyano, nitro, hydroxy, amino or acetamido and wherein $R^3$ is such that $R^3$—$NH_2$ is L-glutamic acid, glycine, L-phenylalanine, L-serine, L-ornithine or L-aspartic acid.

5. A pharmaceutical composition as claimed in claim 1
wherein $R^1$ is methyl, ethyl, methoxy, fluoromethyl or hydroxymethyl;
wherein $R^2$ is hydrogen, methyl, ethyl, propyl, prop-2-enyl, prop-2-ynyl or 2-hydroxyethyl;
wherein Ar is 1,4-phenylene or thien-2,5-diyl and wherein $R^3$ is such that $R^3$—$NH_2$ is L-glutamic acid.

6. A pharmaceutical composition as claimed in claim 1
wherein $R^1$ is methyl, methoxy, fluoromethyl or hydroxymethyl;
wherein $R^2$ is hydrogen, methyl, ethyl, prop-2-ynyl, 3-hydroxypropyl, 2-fluoroethyl or acetonyl;
wherein Ar is 1,4-phenylene, thien-2,5-diyl, pyrid-2,5-diyl or 2-fluoro-1,4-phenylene and wherein $R^3$ is such that $R^3$—$NH_2$ is L-glutamic acid.

7. A pharmaceutical composition as claimed in claim 1
wherein the quinazoline is N-p-[N-(3,4-dihydro-2-methyl-4-oxoquinazolin-6-ylmethyl)-N-(prop-2-ynyl)amino]benzoyl-L-glutamic acid.

8. A pharmaceutical composition as claimed in claim 1
wherein the quinazoline is N-p-[N-(3,4-dihydro-2-methyl-4-oxoquinazolin-6-ylmethyl)-N-ethylamino]-o-fluorobenzoyl-L-glutamic acid.

9. A pharmaceutical composition as claimed in claim 1
wherein the quinazoline is N-{5-[N-(3,4-dihydro-2-methyl-4-oxoquinazolin-6-ylmethyl)-N-methylamino]-2-thenoyl}-L-glutamic acid, 10. A pharmaceutical composition as claimed in claim 1
wherein the quinazoline is selected from the group consisting of:
N-p-[N-(3,4-dihydro-2-methyl-4-oxoquinazolin-6-ylmethyl)-N-methylamino]benzoyl-L-glutamic acid,
N-p-[N-(2-ethyl-3,4-dihydro-4-oxoquinazolin-6-ylmethyl)-N-(prop-2-ynyl)amino]benzoyl-L-glutamic acid,
N-p-[N-(3,4-dihydro-2-methyl-4-oxoquinazolin-6-ylmethyl)-N-methylamino]-o-fluorobenzoyl-L-glutamic acid,
N-p-[N-(3,4-dihydro-2-methyl-4-oxoquinazolin-6-ylmethyl)-N-ethylamino]-o-fluorobenzoyl-L-glutamic acid,
N-p-[N-(3,4-dihydro-2-methyl-4-oxoquinazolin-6-ylmethyl)-N-(prop-2-ynyl)amino]-o-fluorobenzoyl-L-glutamic acid;
N-{5-[N-(3,4-dihydro-2-methyl-4-oxoquinazolin-6-ylmethyl)-N-methylamino]-2-thenoyl}-L-glutamic acid,
N-{5-[N-(3,4-dihydro-2-methyl-4-oxoquinazolin-6-ylmethyl)-N-ethylamino]-2-thenoyl}-L-glutamic acid,
N-{5-[N-(3,4-dihydro-2-methyl-4-oxoquinazolin-6-ylmethyl)-N-(prop-2-ynyl)amino]picolinoyl}-L-glutamic acid,
N-p-[N-(3,4-dihydro-2-methyl-4-oxoquinazolin-6-ylmethyl)-N-(2-fluoroethyl)amino]benzoyl-L-glutamic acid, N-p-[N-(3,4-dihydro-2-methoxy-4-oxoquinazolin-6-ylmethyl)-N-(prop-2-ynyl)amino]benzoyl-L-glutamic acid,
N-p-[N-(3,4-dihydro-2-hydroxymethyl-4-oxoquinazolin-6-ylmethyl)-N-(prop-2-ynyl)amino]benzoyl-L-glutamic acid,
N-p-[N-(3,4-dihydro-2-hydroxymethyl-4-oxoquinazolin-6-ylmethyl)-N-ethylamino]benzoyl-L-glutamic acid,
N-p-[N-(2-fluoromethyl-3,4-dihydro-4-oxoquinazolin-6-ylmethyl)-N-(prop-2-ynyl)amino]benzoyl-L-glutamic acid or
N-p-[N-(2-fluoromethyl-3,4-dihydro-4-oxoquinazolin-6-ylmethyl)-N-ethylamino]benzoyl-L-glutamic acid.

* * * * *

UNITED STATES PATENT AND TRADEMARK OFFICE
CERTIFICATE OF CORRECTION

PATENT NO. : 5,187,167
DATED : Feb. 16, 1993
INVENTOR(S) : Leslie R. Hughes

It is certified that error appears in the above-indentified patent and that said Letters Patent is hereby corrected as shown below:

On title page,
item, [73] Assignee: change "Imperial Chemical Industries PLC, London, England" to --Imperial Chemical Industries, PLC, and National Research Development Corporation, both of London, England--.

Signed and Sealed this

Fifth Day of July, 1994

*Attest:*

BRUCE LEHMAN

*Attesting Officer*     Commissioner of Patents and Trademarks